(12) United States Patent
Corbucci et al.

(10) Patent No.: US 8,437,851 B2
(45) Date of Patent: May 7, 2013

(54) DIAGNOSIS AND THERAPY OF BIGEMINY AND FREQUENT PREMATURE CONTRACTIONS

(75) Inventors: Giorgio Corbucci, Cento (IT); Frank Beckers, Ne Mheer (NL); Guido H. Rieger, Rees (DE)

(73) Assignee: Medtronic, Inc., Minneapolis, MN (US)

( * ) Notice: Subject to any disclaimer, the term of this patent is extended or adjusted under 35 U.S.C. 154(b) by 163 days.

(21) Appl. No.: 12/912,449

(22) Filed: Oct. 26, 2010

(65) Prior Publication Data

US 2012/0101541 A1    Apr. 26, 2012

(51) Int. Cl.
A61N 1/00   (2006.01)
A61N 2/00   (2006.01)
A61N 5/00   (2006.01)

(52) U.S. Cl.
USPC ............ 607/17; 600/508; 600/515; 600/509; 607/4; 607/9; 607/14

(58) Field of Classification Search .......... 600/508–528; 607/4, 9, 14, 17
See application file for complete search history.

(56) References Cited

U.S. PATENT DOCUMENTS

| | | | |
|---|---|---|---|
| 3,779,237 A | 12/1973 | Goeltz et al. | |
| 4,971,058 A | 11/1990 | Pless et al. | |
| 5,271,411 A | 12/1993 | Ripley et al. | |
| 5,669,391 A | 9/1997 | Williams | |
| 5,819,007 A | 10/1998 | Elghazzawi | |
| 5,978,709 A | 11/1999 | Begemann et al. | |
| 6,058,328 A | 5/2000 | Levine et al. | |
| 6,181,968 B1 | 1/2001 | Limousin | |
| 6,871,089 B2 | 3/2005 | Korzinov et al. | |
| 2003/0176795 A1 | 9/2003 | Harris et al. | |
| 2004/0092836 A1* | 5/2004 | Ritscher et al. | 600/518 |
| 2004/0215273 A1* | 10/2004 | Van Bolhuis et al. | 607/27 |
| 2005/0159667 A1 | 7/2005 | Korzinov | |
| 2005/0245975 A1* | 11/2005 | Hettrick et al. | 607/9 |
| 2006/0247547 A1 | 11/2006 | Sarkar et al. | |
| 2008/0167567 A1 | 7/2008 | Bashour et al. | |

OTHER PUBLICATIONS

Anan et al., "Arrhythmia analysis by successive RR plotting," Journal of Electrocardiology, Jul. 1990, vol. 23, No. 3, pp. 243-248.*
Baman et al., "Relationship between burden of premature ventricular complexes and left ventricular function," Heart Rhythm 7:865-869, 2010.
Agarwal et al., "Premature Ventricular Complexes and the Risk of Incident Stroke, The Atherosclerosis Risk in Communities (ARIC) Study," Stroke 41:588-593, 2010.
International Search Report and Written Opinion from corresponding PCT application serial No. PCT/US2011/033577 dated Jul. 3, 2012 (10 pages).

* cited by examiner

Primary Examiner — Niketa Patel
Assistant Examiner — Rimi Sahu
(74) Attorney, Agent, or Firm — Michael C. Soldner

(57) ABSTRACT

The disclosure describes techniques for diagnosing premature contractions of a patient's heart. This system may differentiate premature atrial contractions (PACs) and premature ventricular contractions (PVCs) from atrial fibrillation by identifying changes in R-wave intervals, i.e., R-R intervals, on a Lorenz plot, measuring a coupling interval between R-waves, and analyzing a morphology of the premature contractions, e.g., the QRS complex. These techniques may also identify when severe premature contractions, or bigeminy, are present. In response to the type of premature contractions detected, the system may alert a user of the premature contractions and/or deliver cardiac pacing at an increased pacing rate to eliminate the abnormal intrinsic contractions. The system may also adjust the pacing rate and pacing rate duration for persistent premature contractions.

20 Claims, 14 Drawing Sheets

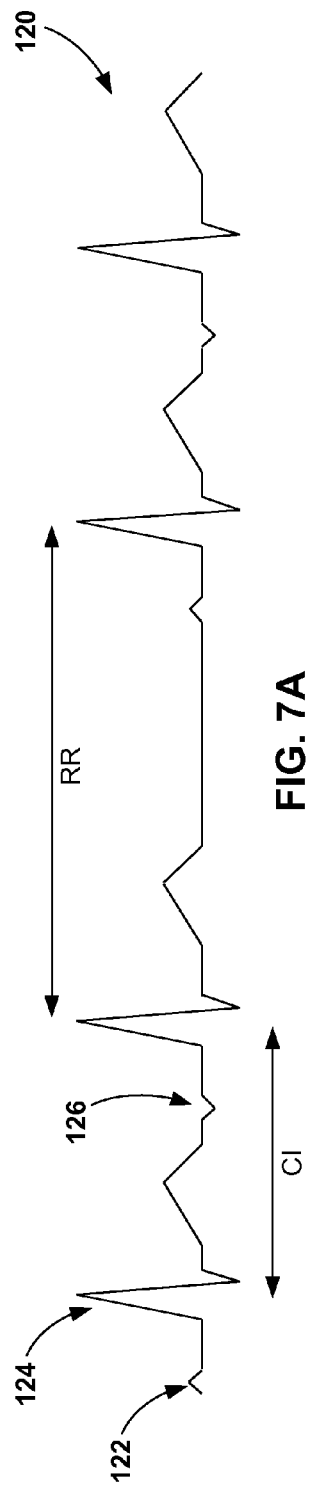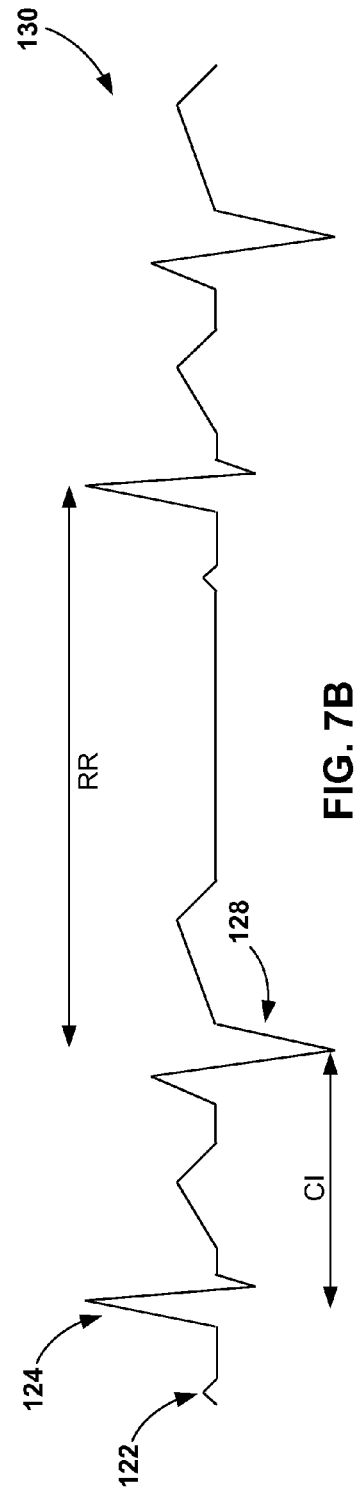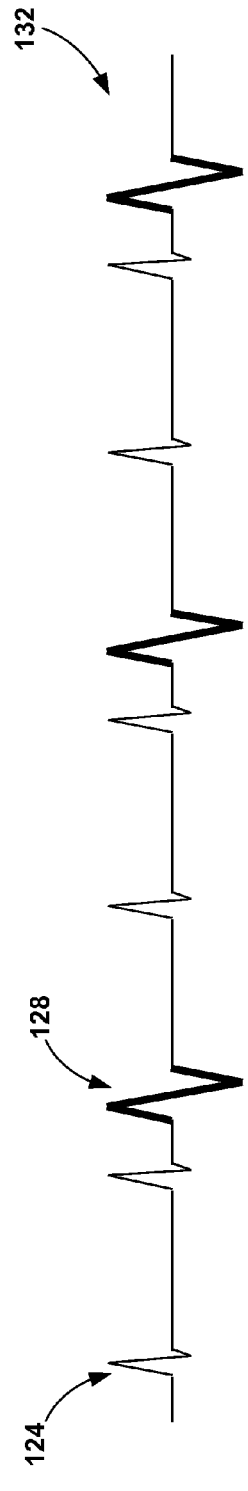

DIAGNOSIS AND THERAPY OF BIGEMINY AND FREQUENT PREMATURE CONTRACTIONS

TECHNICAL FIELD

This disclosure relates to medical devices and, more particularly, to medical devices that monitor physiological conditions of a patient.

BACKGROUND

When functioning properly, a heart maintains its own intrinsic rhythm, and is capable of pumping adequate blood throughout a circulatory system. This intrinsic rhythm is a function of intrinsic signals generated by the sinoatrial node, or SA node, located in the upper right atrium. The SA node periodically depolarizes, which in turn causes the atrial heart tissue to depolarize such that right and left atria contract as the depolarization travels through the atrial heart tissue. The atrial depolarization signal is also received by the atrioventricular node, or AV node, which, in turn, triggers a subsequent ventricular depolarization signal that travels through and depolarizes the ventricular heart tissue causing the right and left ventricles to contract.

Some patients, however, have irregular cardiac rhythms, referred to as cardiac arrhythmias. Cardiac arrhythmias result in diminished blood circulation because of diminished cardiac output. Atrial fibrillation is a common cardiac arrhythmia that reduces the pumping efficiency of the heart. Atrial fibrillation is characterized by rapid, irregular, uncoordinated depolarizations of the atria. In addition to atrial fibrillation, premature contractions of the atria and ventricles can also diminish cardiac output. Frequent premature contractions may be classified as bigeminy, and this condition can lead to symptoms such as palpitations and shortness of breath. For episodes lasting several hours or days, frequent premature contractions may exacerbate other circulatory conditions of the patient. For example, premature contractions of the atria or ventricles can put a patient at increased risk of heart failure. Additionally, frequent premature ventricular contractions may lead to left ventricular dilation and increase the risk of stroke.

SUMMARY

In general, this disclosure is directed to diagnosing and treating premature contractions of a patient's heart. The system described herein may be configured to correctly diagnose and differentiate premature contractions from atrial fibrillation. More specifically, the system may be able to further differentiate between premature atrial contractions (PACs) and premature ventricular contractions (PVCs). A variety of techniques may be used independently, or in combination, to detect premature contractions, including bigeminy, when they occur during cardiac cycles.

One technique utilizes a Lorenz plot of changes in R-wave intervals, i.e., R-R intervals, during the cardiac rhythm to diagnose atrial fibrillation from premature contractions using the degree of variability of cardiac cycle lengths. R-R intervals may be used as one method for determining the cardiac cycle length of each patient heart beat. R-R interval changes due to premature contractions, i.e., a type of cardiac event, are generally clustered in two locations opposite each other and within opposing quadrants of the Lorenz plot. Another technique involves measuring a coupling interval between R-waves, where constant coupling intervals tend to be indicative of frequent premature contractions. In addition the system may analyze a morphology of the cardiac rhythm to identify premature contractions. For example, premature contractions may be present when there are differences between R-wave amplitudes, polarity, and duration among cardiac cycles.

In response to detecting premature contractions in the atria or ventricles, the system may take one or more actions. For example, the system may generate an alert for a user that indicates the type of premature contractions, e.g., PACs, PVCs, or bigeminy, being experienced and the severity of such premature contractions. The alert may even indicate a condition that is of a higher risk, such as frequent PVCs indicating a higher risk of stroke. In addition, or alternatively, the system may provide cardiac stimulation therapy to treat the premature contractions. For example, the system may provide cardiac pacing pulses at a higher rate than a physiological base rate in an attempt to reduce or eliminate the premature contractions from the cardiac rhythm. The system may also adjust the pacing rate or duration for persistent episodes of premature contractions.

In one example, the disclosure provides a method including monitoring a heart of a patient for cardiac cycle lengths, determining a degree of variability of the cardiac cycle lengths, and automatically differentiating premature cardiac events from atrial fibrillation based on the determined degree of variability.

In another example, the disclosure provides a system including an implantable medical device configured to monitor a heart of a patient for cardiac cycle lengths, one or more electrodes coupled to the implantable medical device, and a premature detection module configured to determine a degree of variability of the cardiac cycle lengths and automatically differentiate premature cardiac events from atrial fibrillation based upon to the determined degree of variability.

In another example, the disclosure provides a system including means for monitoring a heart of a patient for cardiac cycle lengths, means for determining a degree of variability of the cardiac cycle lengths, and means for automatically differentiating premature cardiac events from atrial fibrillation based upon the determined degree of variability.

The details of one or more examples are set forth in the accompanying drawings and the description below. Other features, objects, and advantages will be apparent from the description and drawings, and from the claims.

BRIEF DESCRIPTION OF DRAWINGS

FIGS. 7A-C are example timing diagrams of cardiac cycles with premature contractions.

DETAILED DESCRIPTION

Figure 1:
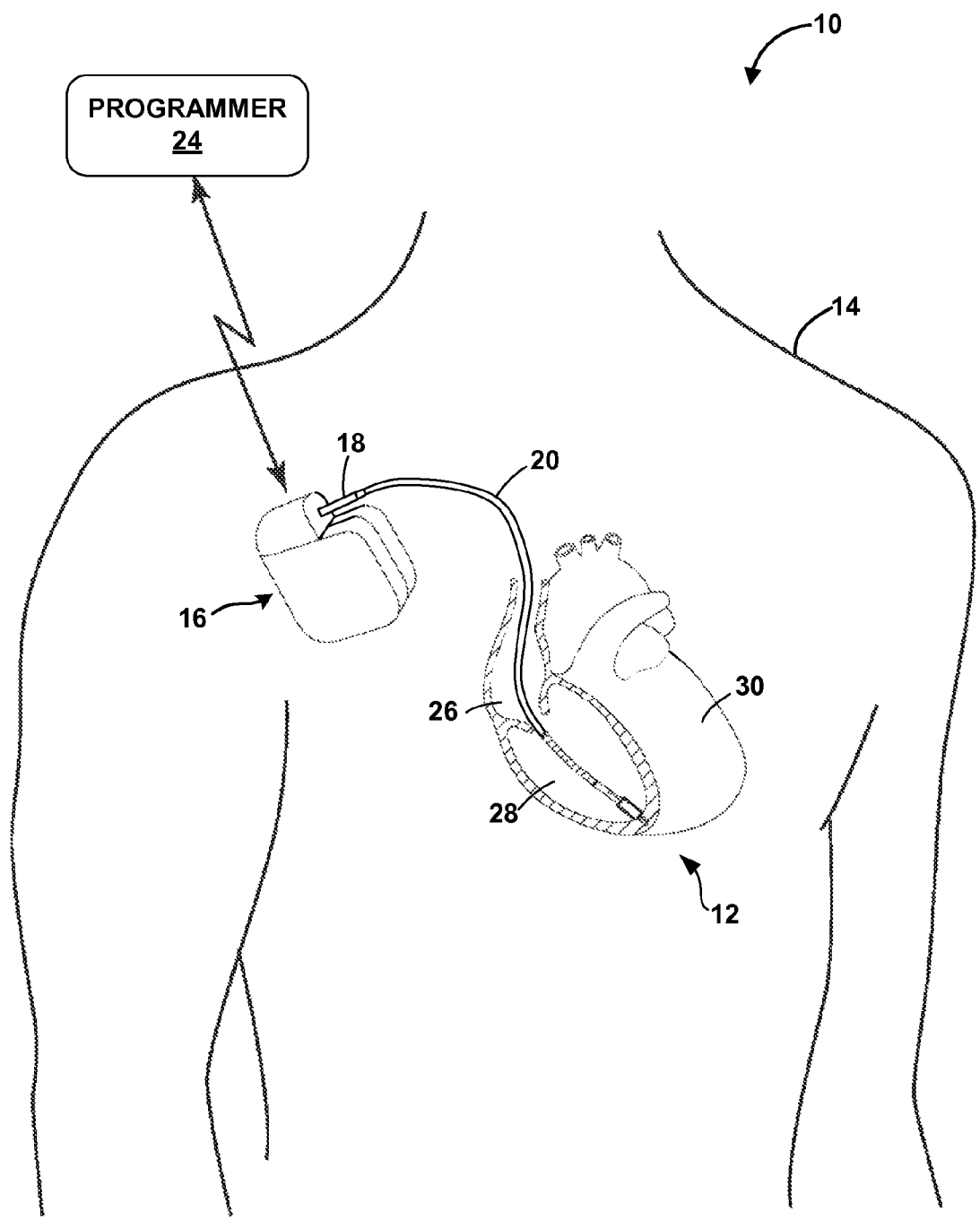
FIG. 1 is a conceptual diagram illustrating an example system comprising an implantable medical device (IMD) that may be used to monitor one or more physiological parameters of a patient and/or provide therapy to the heart of a patient.

In general, this disclosure is directed to diagnosing and treating premature contractions of a patient's heart. When a patient sustains cardiac arrhythmias, correctly diagnosing the specific type of arrhythmia can be beneficial to appropriate treatment of the patient and assessment of future health risks. For example, a diagnosis of atrial fibrillation may indicate that the patient requires cardioversion therapy to restart the normal rhythm of the heart. However, an inaccurate atrial fibrillation diagnosis may result in treatment that damages the patient or fails to remedy the actual cardiac problem. Since premature contractions of the atria or ventricles can be misinterpreted as atrial fibrillation, the techniques and systems described herein are directed to the effective diagnosis of premature contractions and treatment of premature contractions when appropriate.

The system described herein may be configured to correctly diagnose and differentiate premature contractions from atrial fibrillation. More specifically, the system may further differentiate between premature atrial contractions (PACs) and premature ventricular contractions (PVCs). PACs and PVCs are some examples of premature cardiac events that may occur during the cardiac cycle. A variety of techniques may be used independently, or in combination, to detect premature contractions, including bigeminy, when they occur during cardiac cycles. In addition, these techniques may determine when the premature contractions are frequent and the duration of such arrhythmic episodes.

One of these techniques utilizes a Lorenz plot of changes in R-wave intervals, i.e., R-R intervals, during the cardiac rhythm to diagnose premature contractions from a normal sinus rhythm and atrial fibrillation. R-R intervals may be used as one method to determine the cardiac cycle length of consecutive heart beats within the patient. And, changes in R-R intervals may be used to determine a degree of variability of the cardiac cycle lengths. R-R interval changes due to premature contractions are generally clustered in two locations opposite each other, far from the origin, and within opposing quadrants of the Lorenz plot. Although there may be large changes between R-R intervals, the degree of variability for R-R intervals changes is minimal. Conversely, R-R interval changes may have a high degree of variability as the changes are scattered throughout the Lorenz plot. Another technique involves measuring a coupling interval between R-waves. Constant coupling intervals tend to be indicative of frequent premature contractions. In addition the system may analyze the morphology of the QRS complex, e.g., a portion of the cardiac rhythm, to identify premature contractions. For example, premature contractions may be present when there are differences between R-wave amplitudes, polarity, and duration among cardiac cycles. As used herein, a cardiac event may refer to any depolarization or contraction that occurs within the heart of the patient.

In response to detecting premature contractions in the atria or ventricles, the system may take one or more actions. For example, the system may generate an alert for a user that indicates the type of premature contractions, e.g., PACs, PVCs, or bigeminy, being experienced and the severity of such premature contractions. An external programmer or display may present the alert immediately or upon the next interrogation of the implantable medical device (IMD). The alert may even indicate a condition that is of a higher risk, such as frequent PVCs indicating a higher risk of stroke.

In addition, or alternatively, the system may provide cardiac stimulation therapy to treat the premature contractions. For example, the system may provide stimulation therapy in the form of cardiac pacing pulses at a higher rate than a physiological base rate. This higher pacing rate may reduce or eliminate the premature contractions from the patient's cardiac rhythm. The system may also adjust the increased pacing rate and/or duration to treat persistent episodes of premature contractions. In this manner, the techniques described herein may be implemented in any device capable of detecting cardiac cycle lengths and/or delivering electrical stimulation therapy. These devices may include implantable or external medical devices such single chamber pacemakers, dual chamber pacemakers, implantable cardio defibrillators (ICDs), cardiac resynchronization therapy devices, or heart monitors.

FIG. 1 is a conceptual diagram illustrating an example therapy system 10 comprising an implantable medical device (IMD) 16 that may be used to monitor one or more physiological parameters of patient 14 and/or provide therapy to heart 12 of a patient. Therapy system 10 includes IMD 16, which is coupled to lead 20 via connector 18 and programmer 24. IMD 16 may be an implantable pacemaker that provides electrical signals to heart 12 via electrodes coupled to lead 20. In addition to pacing therapy, IMD 16 may deliver AV nodal stimulation and/or neurostimulation signals. In some examples, IMD 16 may also include cardioversion and/or defibrillation functionalities. Although IMD 16 is presented as a single chamber cardiac device in FIG. 1, other examples of IMD 16 may be coupled to two or more leads, each having at least one electrode, to monitor or treat patient 14. When electrodes of leads are placed near or within multiple chambers of heart 12, IMD 16 may be considered a multiple chamber cardiac device. Patient 14 is ordinarily, but not necessarily, is a human patient.

Lead 20 extends into the heart 12 of patient 14 to sense electrical activity of and/or deliver electrical stimulation to the heart. In the example shown in FIG. 1, right ventricular (RV) lead 20 extends through one or more veins (not shown), the superior vena cava (not shown), and right atrium 26, and into right ventricle 28. RV lead 20 may be used to deliver RV pacing to heart 12.

IMD 16 may sense electrical signals attendant to the depolarization and repolarization of heart 12 via electrodes (not shown in FIG. 1) coupled to lead 20 and in some cases with an electrode coupled to the case of IMD 16 (not shown). These sensed signals may be stored within a memory of IMD 16 for later review or use in diagnosing the physiological condition of heart 12. In some examples, IMD 16 provides pacing pulses to heart 12 based on the electrical signals sensed within heart 12. The configurations of electrodes used by IMD 16 for sensing and pacing may be unipolar or bipolar.

IMD 16 may trigger ventricular pacing, based on atrial depolarizations sensed via RV lead 20. In other examples, a lead placed within the right atrium may sense and/or deliver atrial pacing based upon atrial events. In some examples, RV lead 20 may sense ventricular depolarizations, and IMD 16 may trigger ventricular pacing, e.g., RV pacing, based on whether RV lead 20 detects an intrinsic ventricular depolarization within a defined time interval following the atrial sensed or paced event. The time interval between an atrial sensed or paced event and delivery of a pacing pulse to one or more of the ventricles may be referred to as an AV interval. In examples where IMD 16 is coupled to leads placed within the right atrium or left ventricle, any of these leads may be used to sense depolarizations and deliver pacing pulses to their respective chambers of heart 12.

IMD 16 may also provide neurostimulation therapy, defibrillation therapy and/or cardioversion therapy via electrodes located on lead 20 and/or the case of IMD 16. IMD 16 may detect arrhythmia of heart 12, such as fibrillation of ventricles 28 and 30, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 may detect fibrillation employing one or more appropriate fibrillation detection techniques. IMD 16 may similarly deliver anti-tachycardia pacing or cardioversion in response to detecting tachycardia of ventricles 28 and 30.

In accordance with the examples disclosed herein, IMD 16 may also detect premature cardiac events, e.g., contractions of either the atria or ventricles. The electrodes of lead 20, and sometimes the electrode of IMD 16, may be used to sense electrical signals from heart 12. These electrical signals may be used to generate a cardio-electrogram, or internally sensed electrocardiogram (ECG), that indicates the magnitude and timing of depolarizations of cardiac muscle within heart 12. The cardio-electrogram may also be used to monitor the cardiac cycle lengths of each heart beat. IMD 16 may then distinguish premature contractions from atrial or ventricular fibrillation using a degree of variability of the cardiac cycle lengths. Further, IMD 16 may differentiate PACs from PVCs to pursue the most appropriate form of therapy for patient 14.

For example, IMD 16 may generate a Lorenz plot of R-R interval changes between consecutive cardiac cycles to diagnose premature cardiac events, e.g., atrial or ventricular contractions, from fibrillation, e.g., atrial fibrillation. The R-wave is the depolarization of the ventricles and may be used to determine the cardiac cycle length of each cardiac cycle. In atrial fibrillation, for example, the R-R interval change is sporadic, leaving plots spread out over the Lorenz plot. Conversely, premature contractions, e.g., bigeminy, produce a generally consistent change in R-R interval between normal R-waves and the R-waves of premature contractions. This consistent R-R interval change is generally consistent whether a PAC or a PVC occurs, but the R-R interval change may be different between PACs and PVCs. In the Lorenz plot, premature contractions produce R-R interval changes located far from the origin, in opposing quadrants. While normal sinus rhythm R-R interval changes are populate near the origin, R-R interval changes for atrial fibrillation scatter throughout the Lorenz plot. By identifying these differences, a user may analyze the Lorenz plot to differentiate premature contractions from fibrillation in heart 12. Although not presented, IMD 16 may also analyze the R-R interval changes used in a Lorenz plot to similarly differentiate between premature contractions and atrial fibrillation by determining a degree of variability in cardiac cycle lengths.

IMD 16 may also utilize a measured coupling interval to differentiate premature contractions from fibrillation. The coupling interval is the duration of time between the R-wave of a normal contraction and the R-wave of the premature contraction, in either PACs or PVCs. When the coupling interval is irregular, atrial fibrillation is likely occurring. A constant coupling interval indicates that premature contractions are occurring during the cardiac rhythm. Coupling intervals may be analyzed over a predetermined time window, such as a time window of two to ten minutes, for example. A constant coupling interval during this time window may indicate that the cardiac rhythm includes premature contractions, or bigeminy, instead of atrial fibrillation.

IMD 16 may also consider the morphology of the R-wave to determine whether the premature contractions are PACs or PVCs. PACs have R-waves of similar amplitude, polarity, and duration. In contrast, cardiac rhythms with PVCs typically include R-waves with different amplitudes, different polarities, and different durations. Since IMD 16 may provide different treatments whether the premature contractions are atrial or ventricular, analyzing the morphology of the R-waves may be beneficial to the diagnosis.

IMD 16 may also provide cardiac stimulation therapy for premature contractions depending upon their type and/or severity. Although the stimulation therapy may be in the form of defibrillation or cardioversion, IMD 16 may generally provide pacing pulses to heart 12 to treat premature contractions, e.g., PACs or PVCs. When premature contractions are infrequent or otherwise inconsequential to the health of patient 14, IMD 16 may not deliver any therapy. However, frequent premature contractions, e.g., bigeminism, may be effectively treated by providing cardiac pacing therapy.

Generally, treatment for premature contractions may include increasing the normal pacing rate, i.e., the prescribed pulse rate, intrinsic heart rate, or base rate, so that premature depolarizations in the cardiac tissue are eliminated. For example, the increased pacing rate may be set at 5 beats per minute (bpm) above the base rate. However, the base rate may generally be increased from 1 bpm to 20 bpm or higher. IMD 16 may limit the increased pacing rate to a maximum pacing rate set by a clinician. This increased or elevated pacing rate may be delivered for a preset duration or until IMD 16 no longer senses any premature contractions. For example, the preset duration may be 10 minutes. In other examples, the preset duration may be a shorter duration or a longer duration of up to hours, days, or even weeks.

In some cases of persistent premature contractions, IMD 16 may incrementally increase the pacing rate until the premature contractions cease or a maximum heart rate is reached. For example, IMD 16 may increase the elevated pacing rate by 5 bpm after each duration of elevated pacing that is ineffective in eliminating premature contractions. The completion of a single duration may be identified as a treatment cycle. Alternatively, the increments may be exponential to reach an effective pacing rate within fewer treatment cycles. In other examples, the incremental increases in pacing rate may be set based upon the frequency of the remaining premature contractions. In other words, more frequent premature contractions may be treated with a higher pacing rate.

Instead of, or in addition to, incrementally increasing the pacing rate, IMD 16 may incrementally increase the pacing rate duration after each ineffective treatment cycle. For example, the increased pacing rate may be initially set to 5 bpm above the base rate for 10 minutes. After the treatment cycle, and upon continued detection of the premature contractions, IMD 16 may start another treatment cycle with the same elevated pacing rate for a longer duration, e.g., 20 minutes. IMD 16 may continue to increase the duration until the premature contractions cease or patient 14 should no longer be subjected to the increased pacing rate.

In alternative examples, IMD 16 or another implantable medical device may deliver a bolus or stream of drugs to remedy the PACs or PVCs. Any drug provided to patient 14 may be directed to rectifying the uncoordinated depolarizations of cardiac tissue within heart 12. Further, the drug may be delivered in addition to cardiac pacing therapy.

Referring again to FIG. 1, programmer 24 comprises a handheld computing device, computer workstation, networked computing device, or other external device. Programmer 24 includes a user interface that presents information to and receives input from a user. It should be noted that the user may also interact with programmer 24 remotely via a networked computing device.

A user, such as a physician, technician, surgeon, electrophysiologist, or other clinician, interacts with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD. In some examples, patient 14 may interact with programmer 24 to view physiological information, select a desired therapy, or provide input regarding symptoms or other activity related to the therapy or health of patient 14.

In one example, a user may retrieve information regarding the rhythm of heart 12, trends therein over time, arrhythmic episodes, premature contraction diagnosis, or other therapy information from IMD 16 using programmer 24. As another example, the user may use programmer 24 to retrieve information from IMD 16 regarding other sensed physiological parameters of patient 14 or information derived from sensed physiological parameters, such as the heart rate during premature contractions or activity of patient 14 during diagnosis or therapy. As another example, the user may use programmer 24 to retrieve information from IMD 16 regarding the performance or integrity of IMD 16 or other components of system 10, such as lead 20, or a power source of IMD 16. As another example, the user may interact with programmer 24 to program, e.g., select parameters for, therapies provided by IMD 16, such as AV nodal vagal stimulation and, optionally, cardioversion and/or defibrillation. In one example, the user employs programmer 24 to program IMD 16 with therapies for detected PACs and PVCs and parameters for each of these therapies.

In addition, programmer 24 may provide information about detected premature contractions or even provide alerts when patient 14 is undergoing premature contractions. For example, programmer 24 may provide an alert when IMD 16 is interrogated. Alternatively, IMD 16 may actively push an alert to programmer 24 when the premature contractions need to be treated or patient 14 needs immediate medical attention.

IMD 16 and programmer 24 may communicate via wireless communication using a number of appropriate techniques including, e.g., low frequency or radiofrequency (RF) telemetry, but other techniques are also contemplated. In some examples, programmer 24 includes a programming head that may be placed proximate to the patient's body near the IMD 16 implant site in order to improve the quality or security of communication between IMD 16 and programmer 24.

Although IMD 16 may be a single chamber pacemaker, IMD 16 may be any type of implanted or external device capable of monitoring cardiac cycle lengths to detect premature cardiac events. For example, other examples of IMD 16 may include implantable or external devices such dual chamber pacemakers, implantable cardio defibrillators (ICDs), cardiac resynchronization therapy devices (e.g., triple chamber CRTs), or heart monitors.

Figure 2:
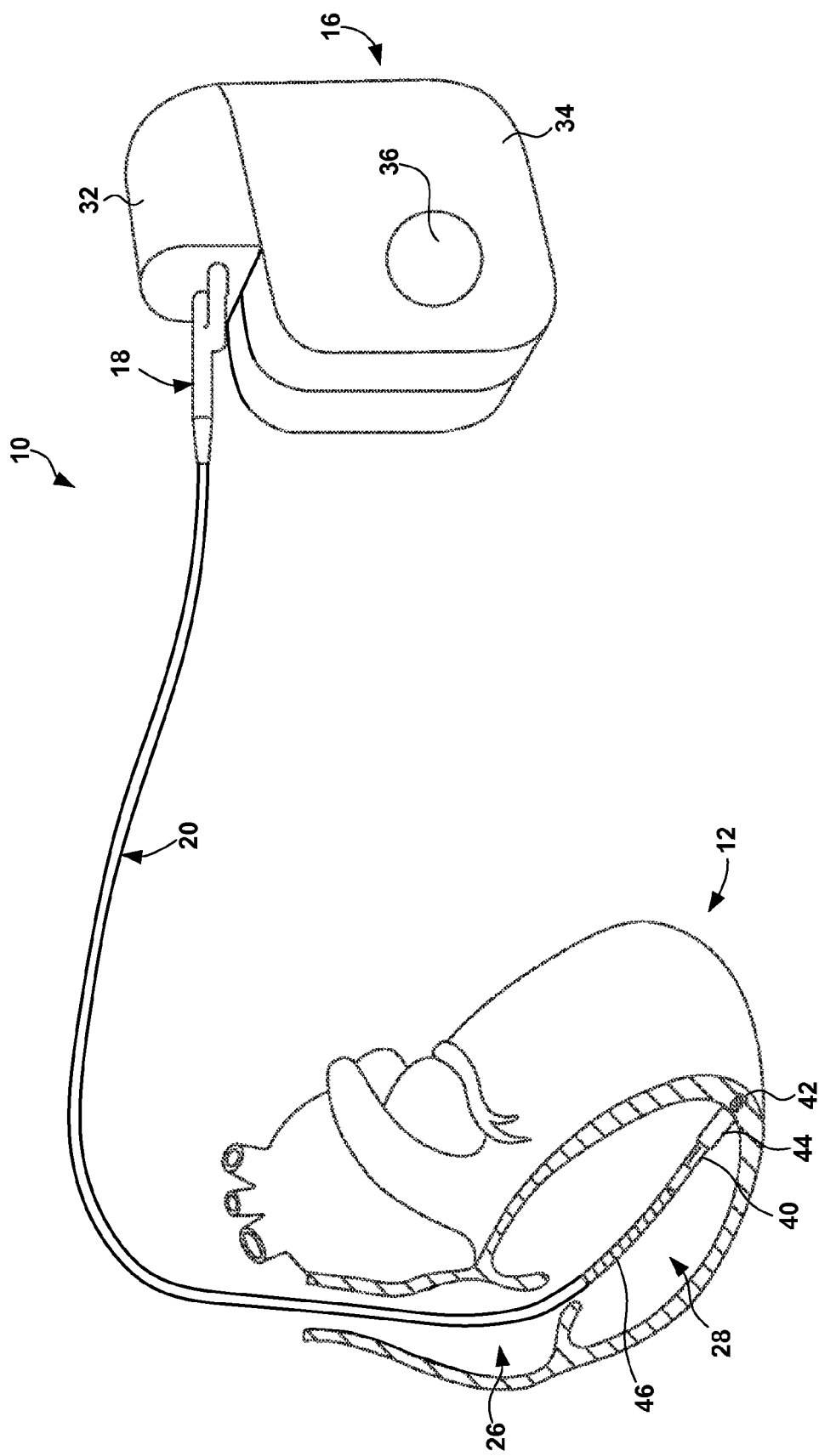
FIG. 2 is a conceptual diagram further illustrating the IMD and lead of the system of FIG. 1 in conjunction with the heart.

FIG. 2 is a conceptual diagram further illustrating IMD 16 and lead 20 of therapy system 10 of FIG. 1 in greater detail. Lead 20 may be electrically coupled to a signal generator and a sensing module of IMD 16 via connector 18 electrically coupled to connector block 32. In the example of FIG. 2, the proximal end of lead 20 includes connector 18 that includes electrical contacts that electrically couple to respective electrical contacts within connector 32 of IMD 16. In addition, in some examples, lead 20 may be mechanically coupled to connector block 32 with the aid of set screws, connection pins, snap connectors, or another suitable mechanical coupling mechanism.

Lead 20 includes an elongated insulative lead body, which may carry a number of concentric coiled conductors separated from one another by tubular insulative sheaths. Bipolar electrodes 40 and 42 are located adjacent to a distal end of lead 20 in right ventricle 28. Electrode 40 may take the form of a ring electrode, and electrode 42 may take the form of an extendable helix tip electrode mounted retractably within insulative electrode head 44. In some examples, electrode 42 may take the form of a pre-exposed helix tip electrode. In other examples, electrode 42 may take the form of a small circular electrode at the tip of a tined lead or other fixation element. Lead 20 also includes elongated electrode 46 which may take the form of a coil. Each of the electrodes 40, 42, and 46 may be electrically coupled to a respective one of the coiled conductors within the lead body of lead 20 and thereby coupled to respective ones of the electrical contacts of connector 18 on the proximal end of lead 20.

In some examples, as illustrated in FIG. 2, IMD 16 includes one or more housing electrodes, such as housing electrode 36, which may be formed integrally with an outer surface of hermetically-sealed housing 34 of IMD 16 or otherwise coupled to housing 34. In some examples, housing electrode 36 is defined by an uninsulated portion of an outward facing portion of housing 34 of IMD 16. Other division between insulated and uninsulated portions of housing 34 may be employed to define two or more housing electrodes. In some examples, housing electrode 36 comprises substantially all of housing 34. As described in further detail with reference to FIG. 4, housing 34 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 46, and 36. The electrical signals are conducted to IMD 16 from the electrodes via the lead 20, or in the case of housing electrode 36, a conductor coupled to housing electrode 36. IMD 16 may sense such electrical signals via any bipolar combination of electrodes 40, 42, 46, and 36. Furthermore, any of the electrodes 40, 42, and 46 may be used for unipolar sensing in combination with housing electrode 36.

In some examples, IMD 16 delivers pacing pulses via bipolar combinations of electrodes 40 and 42 to produce depolarization of cardiac tissue of heart 12. In some examples, IMD 16 delivers pacing pulses via any of electrodes 40 and 42 in combination with housing electrode 36 in a unipolar configuration. For example, electrodes 40, 42, and/or 46 may be used to deliver RV pacing to heart 12. Furthermore, IMD 16 may deliver defibrillation shocks to heart 12 via elongated electrode 46 and housing electrode 36. Electrodes 36 and 46 may also be used to deliver cardioversion shocks to heart 12. Although pacing, cardioversion, defibrillation, or any electrical stimulation or shocks may be in the form of pulses, other types of signals may also be used in some examples. Electrode 46 may be fabricated from any suitable electrically conductive material, such as, but not limited to, platinum, platinum alloy or other materials known to be usable in implantable defibrillation electrodes.

According to the techniques herein, any of electrodes 42, 44, 46, and housing electrode 36 may be used to sense the rhythm of heart 12. IMD 16 may identify R-waves and other rhythm characteristics within signals sensed by the electrodes to differentiate between atrial fibrillation, PACs, and PVCs. Based upon the diagnosed condition of the heart 12 rhythm, a specific bipolar or unipolar combination of electrodes 42, 44, 46, and 36 may be used to provide cardiac pacing therapy, defibrillation, or other stimulation therapy to treat patient 14. Although these detection and therapy techniques may be used as shown in FIG. 2 in a single chamber cardiac device, dual chamber or multiple chamber cardiac devices may be used to similarly diagnose and treat PACs and PVCs.

The configuration of therapy system 10 illustrated in FIGS. 1 and 2 is merely one example. In other examples, a therapy system may include epicardial leads and/or patch electrodes instead of or in addition to the transvenous lead 20 illustrated in FIG. 1. Further, IMD 16 need not be implanted within patient 14. In examples in which IMD 16 is not implanted in patient 14, IMD 16 may deliver pacing and defibrillation pulses and other therapies to heart 12 via percutaneous leads that extend through the skin of patient 14 to a variety of positions within or outside of heart 12.

In addition, in other examples, a therapy system may include any suitable number of leads coupled to IMD 16, and each of the leads may extend to any location within or proximate to heart 12. For example, other examples of therapy systems may include one transvenous leads located as illustrated in FIGS. 1 and 2, and an additional lead located within or proximate to right atrium 26 or the left atrium or ventricle. As another example, other examples of therapy systems may include a two leads that extend from IMD 16 into right atrium 26 and right ventricle 28, or three leads that extend into right ventricle 26, right atrium 26, and the left ventricle.

Figure 3:
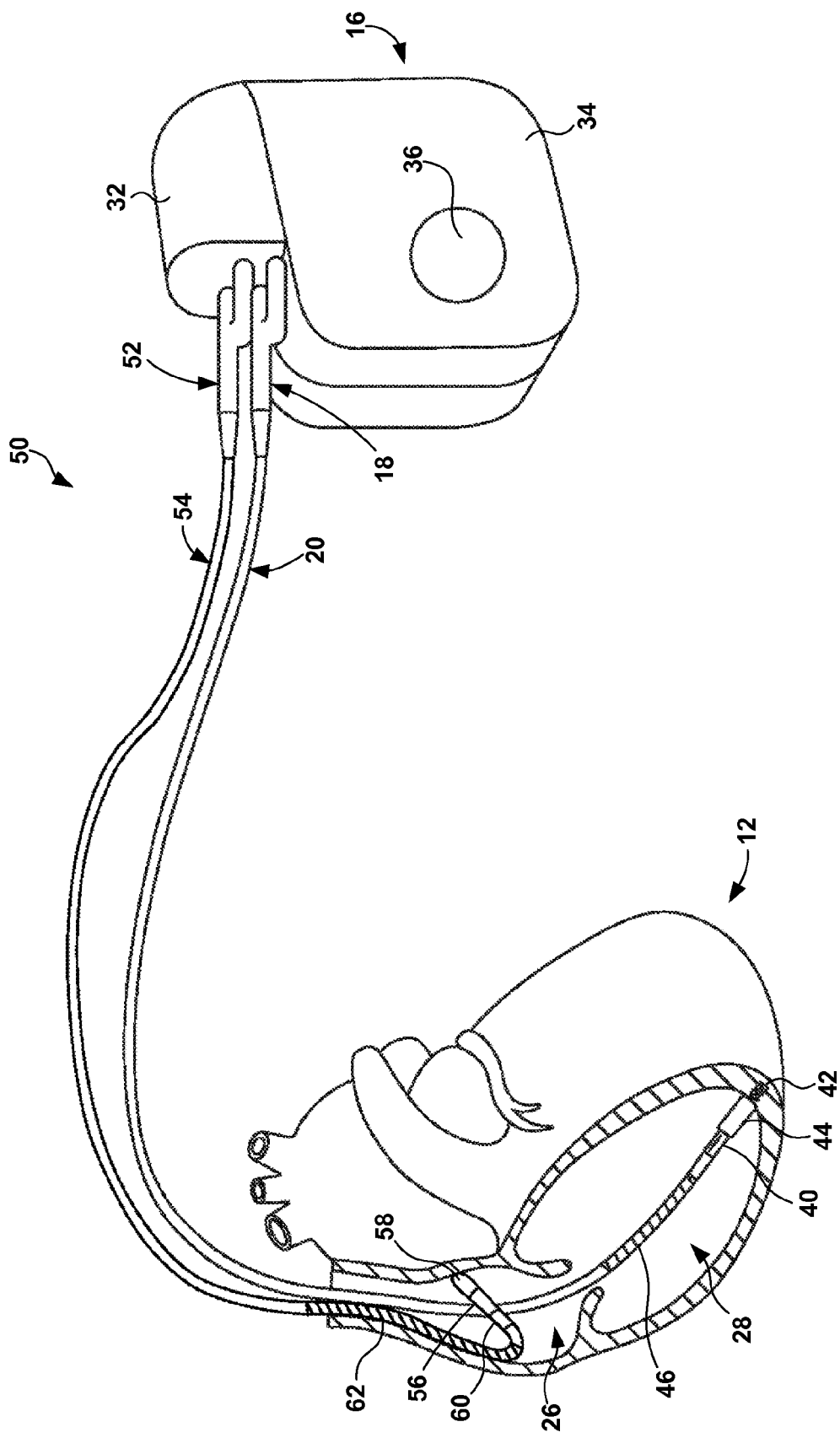
FIG. 3 is a conceptual diagram further illustrating a dual chamber IMD with two leads placed in different chambers of the heart.

FIG. 3 is a conceptual diagram further illustrating another therapy system 50 similar to the therapy system 10 if FIGS. 1 and 2. However, therapy system 50 is a dual chamber cardiac system that includes IMD 16 coupled to two leads 20 and 54 rather than a single lead 20. Leads 20 and 54 are implanted within right ventricle 28 and right atrium 26, respectively. Therapy system 50 shown in FIG. 3 may be useful for providing pacing pulses and cardioversion-defibrillation shocks to heart 12, and for providing any of functionality described in this disclosure with respect to the systems of FIGS. 1-2. For example, system 50 may be configured to diagnose premature contractions and identify PACs and PVCs similar to system 10.

RA lead 54 also includes electrodes 58, 60, and 62. Tip electrode 58 may be a small circular electrode placed against the tissue of right atrium 26 or an insertable electrode. In other words, tip electrode 58 may be a helix that is extendable or pre-exposed to be inserted into the tissue of right atrium 26 to substantially fix RA lead 54 within right atrium 26. Right atrial (RA) lead 54 extends through one or more veins and the vena cava, and into the right atrium 26 of heart 12. RA lead 54 may be positioned in the inferior portion of right atrium 26. In some examples, RA lead 54 may be positioned in the posterior portion of right atrium 26 around the coronary sinus ostium, such as posteriorly to the coronary sinus ostium, and along the septum that separates right atrium 26 from the left atrium (not shown). For example, RA lead 54 may be positioned such that RA lead 54 may sense electrical activity within right atrium 26, pace right atrium 26, and also deliver a stimulation signal to or proximate to the AV node, e.g., to or proximate to the AV nodal vagal fat pad.

In some alternative examples, therapy system 50 may include an additional lead or lead segment (not shown in FIG. 1) that deploys one or more electrodes within the vena cava or other vein, or within or near the aorta. In other alternative examples, system 50 may include one or more additional intravenous or extravascular leads or lead segments that deploy one or more electrodes epicardially. In other alternative examples, system 50 may include another lead within the left ventricle to provide pacing therapy to both the left and right ventricles.

For example, a left ventricular lead (LV lead) may be used in combination with RV lead 20 to deliver biventricular pacing to heart 12, which may provide cardiac resynchronization therapy (CRT) to heart 12. CRT may be used to treat heart failure-inducted conduction disturbances and/or ventricular dyssynchrony. This may include treatment for premature contractions within heart 12. In some cases, CRT may help restore the mechanical sequence of ventricular activation and contraction. Additionally, CRT may involve biventricular pacing, e.g., via RV lead 20 and the LV lead, to synchronize the contraction of both ventricles. In other examples, CRT may involve pacing one of the ventricles, e.g., the left ventricle via the LV lead, to synchronize its contraction with that of the other ventricle.

Figure 4:
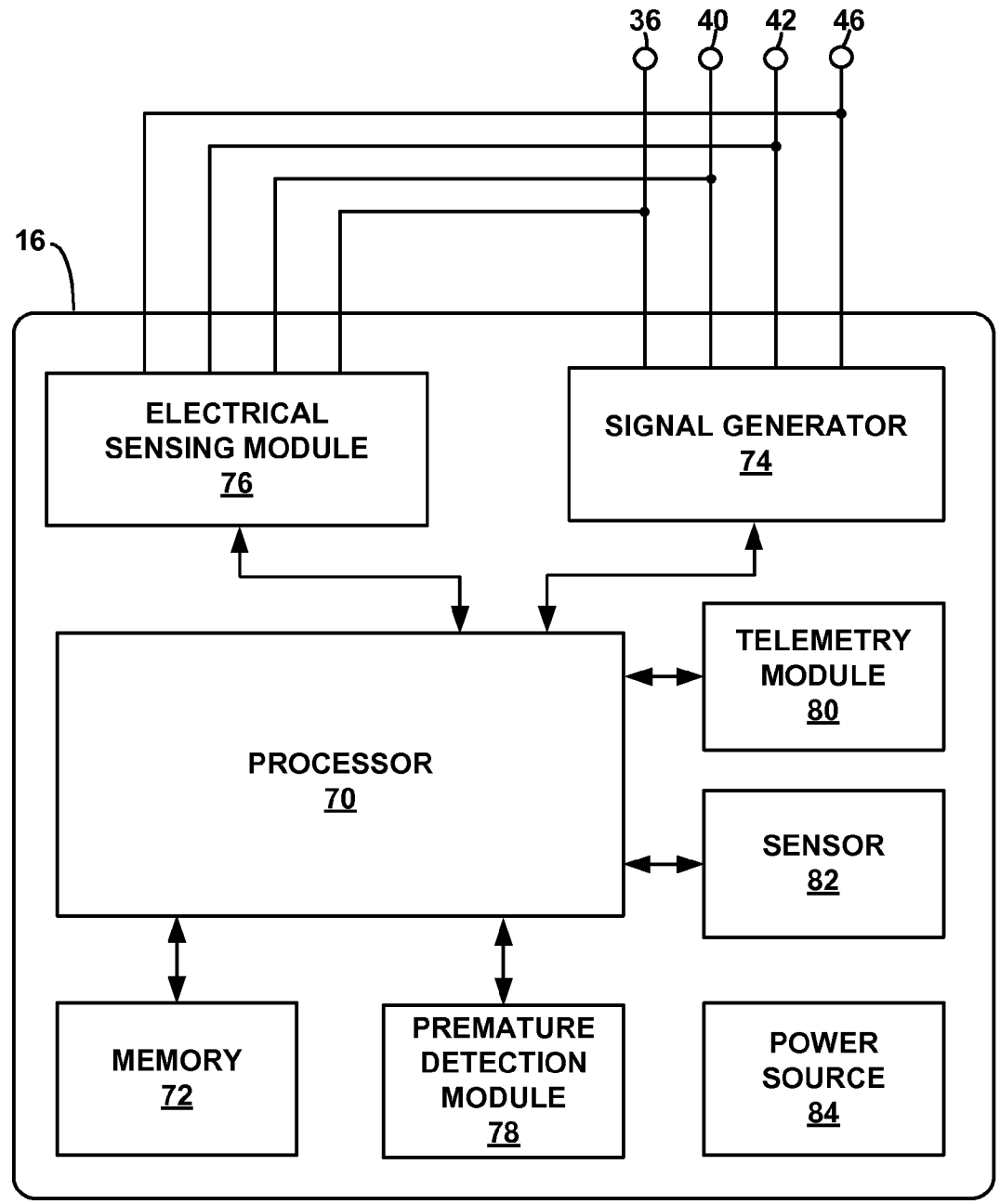
FIG. 4 is a functional block diagram illustrating an example configuration of an IMD.

FIG. 4 is a functional block diagram illustrating one example configuration of IMD 16 including processor 70, memory 72, signal generator 74, electrical sensing module 76, premature detection module 78, sensor 82, telemetry module 80, and power source 84. Memory 72 may include computer-readable instructions that, when executed by processor 70, cause IMD 16 and processor 70 to perform various functions attributed to IMD 16 and processor 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 70 may include any one or more of a microprocessor, a controller, a digital signal processor (DSP), an application specific integrated circuit (ASIC), a field-programmable gate array (FPGA), or equivalent discrete or integrated logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof. Processor 70 controls signal generator 74 to deliver stimulation therapy to heart 12 according to operational parameters or programs, which may be stored in memory 72.

Signal generator 74 is electrically coupled to electrodes 36, 40, 42, 44, and 46, e.g., via conductors of the respective lead 20 or, in the case of housing electrode 36, via an electrical conductor disposed within housing 34 of IMD 16. Signal generator 74 is configured to generate and deliver electrical stimulation therapy to heart 12. For example, signal generator 74 may deliver defibrillation shocks to heart 12 via electrodes 36 and 46. Signal generator 74 may also deliver pacing pulses via ring electrode 40 coupled to lead 20 and/or helical electrodes 42 of lead 20. In some examples, signal generator 74 delivers one or more of these types of stimulation in the form of electrical pulses. In other examples, signal generator 74 may deliver one or more of these types of stimulation in the form of other signals, such as sine waves, square waves, or other substantially continuous time signals.

Memory 72 may store values for stimulation parameters that processor 70 accesses to control delivery of cardiac stimulation therapy, e.g., pacing therapy or defibrillation therapy, by signal generator 74. Such stimulation parameters may include pulse duration, pulse amplitude, and pacing rate, e.g., the value of one or more escape intervals. As one example, signal generator 74 may control stimulation using a pulse duration of approximately 0.1 to 5.0 milliseconds, an amplitude of approximately 0.5 to 8 volts, and a pulse frequency of approximately 40 to 130 pulses per minute (ppm) if needed to maintain a predetermined heart beat frequency. These values merely are examples and other values are also contemplated.

In some examples, memory 72 may store other operation parameters of IMD 16 by which IMD 15 diagnoses premature contractions from the cardiac rhythm and treats the premature contractions. For example, memory 72 may store values of parameters related to as well as instructions for detecting and analyzing R-waves within an electrocardiogram to diagnose PACs and PVCs. An example diagnostic parameter may include a premature contraction threshold which indicates pacing therapy is required when the PACs or PVCs become too frequent. Memory 72 may also store instructions for generating and interpreting Lorenz plots of R-R interval changes.

In some examples, memory 72 may also store suitable ranges for one or more stimulation parameters. As one example, memory 72 stores a pulse duration, e.g., pulse width, range of approximately 0.1 milliseconds to approximately 5.0 milliseconds. In other examples, the pulse frequency may fall outside of this range. In another example, memory 72 stores an amplitude range of approximately 0.5 volts to approximately 8 volts.

Signal generator 74 may include a switch module and processor 70 may use the switch module to select, e.g., via a data/address bus, which of the available electrodes are used to deliver stimulation signals, e.g., defibrillation or pacing stimulation signals. The switch module may include a switch array, switch matrix, multiplexer, or any other type of switching device suitable to selectively couple a signal to selected electrodes.

Electrical sensing module 76 monitors signals from at least one of electrodes 40, 42, 46, and 36 in order to monitor electrical activity of heart 12. In this manner, sensing module 76 is a means for monitoring depolarization timing of patient 14. Electrical sensing module 76 may also include a switch module to select which of the available electrodes are used to sense heart 12 activity. In some examples, processor 70 may select the electrodes that function as sense electrodes, or the sensing configuration, via the switch module within electrical sensing module 76, e.g., by providing signals via a data/address bus.

In some examples, electrical sensing module 76 includes multiple detection channels, each of which may comprise an amplifier. Each sensing channel may detect electrical activity in respective chamber of heart 12, and may be configured to detect either R-waves or P-waves. In some examples, electrical sensing module 76 or processor 70 may include an analog-to-digital converter for digitizing the signal received from a sensing channel for electrogram signal processing by processor 70. In response to the signals from processor 70, the switch module within electrical sensing module 76 may couple the outputs from the selected electrodes to one of the detection channels or the analog-to-digital converter.

During pacing, escape interval counters maintained by processor 70 may be reset upon sensing of R-waves and P-waves with respective detection channels of electrical sensing module 76. Signal generator 74 may include pacer output circuits that are coupled, e.g., selectively by a switching module, to any combination of electrodes 40, 42, 46, and 36 appropriate for delivery of a bipolar or unipolar pacing pulse to one or more of the chambers of heart 12. Processor 70 may control signal generator 74 to deliver a pacing pulse to a chamber upon expiration of an escape interval. Processor 70 may reset the escape interval counters upon the generation of pacing pulses by signal generator 74, or detection of an intrinsic depolarization in a chamber, and thereby control the basic timing of cardiac pacing functions. The escape interval counters may include P-P, V-V, RV-LV, A-V, A-RV, or A-LV interval counters, as examples. The value of the count present in the escape interval counters when reset by sensed R-waves and P-waves may be used by processor 70 to measure the durations of R-R intervals, P-P intervals, P-R intervals and R-P intervals. Processor 70 may use the count in the interval counters to detect a tachyarrhythmia event, such as an atrial or ventricular fibrillation or tachycardia and/or detect a heart rate, such as an atrial rate or ventricular rate. For example, processor 70 may measure and record a number of P-P intervals and R-R intervals for heart 12, from which the processor may detect an atrial tachyarrhythmia by detecting a median P-P interval in heart 12 of patient 14 that is less than a percentage threshold of a median R-R interval of the heart. Processor 70 may also use the detected R-R intervals to differentiate premature contractions from atrial fibrillation and PACs from PVCs.

Processor 70 may also derive other physiological parameters from signals sensed via electrical sensing module 76. For example, processor 70 may establish one or more indicators of ejection fraction and/or heart failure status from electrical signals sensed via electrical sensing module 76. In particular, impedance signals may be used to determine flow or pressure, which may indicate ejection fraction and/or heart failure status.

In one example, premature detection module 78, in conjunction with memory 72, signal generator 74, and sensing module 76 detects characteristics of the electrical activity, and rhythm, of heart 12 to detect and diagnose premature contractions. Premature detection module 78 may continuously monitor heart 12 for the contraction timing, or cardiac rhythm, or heart 12 and analyze cardio-electrogram data stored in memory 72, or otherwise analyze cardiac information to detect premature contractions occurring in real-time or that have occurred in the past.

Premature detection module 78 may be programmed to control, or instruct processor 70 to control, sensing module 76 to sense the cardio-electrogram of heart 12. With information from sensing module 76, premature detection module 78 may monitor cardiac cycle lengths and determine a degree of variability of the cardiac cycle lengths. Premature detection module 78 may monitor cardiac cycle lengths by measuring the R-R interval. Premature detection module 78 may also determine the degree of variability of the cardiac cycles by calculating changes between R-R intervals, and in some examples, generating a Lorenz plot. By analyzing the Lorenz plot, or analyzing the variation of changes between R-R intervals in the cardio-electrogram, premature detection module 78 may identify arrhythmias and differentiate premature contractions from atrial fibrillation. Premature detection module 78 may also analyze the morphology of R-waves to identify differences in R-wave amplitudes, polarity, and duration. Further, premature detection module 78 may measure the duration between consecutive R-waves to calculate coupling intervals that suggest whether the arrhythmia is atrial fibrillation or premature contractions. R-wave frequency can also be used by premature detection module 78 to indicate how frequent the premature contractions are occurring in the rhythm. In some examples, premature detection module 78 may include an R-wave detector that produces R-wave markers in time for use in generating R-R intervals and coupling intervals.

In this manner, premature detection module 78 may be responsible for detecting PACs and PVCs in the rhythm of heart 12, e.g., a means for identifying contraction variability and differentiating premature contractions from atrial fibrillation. Premature detection module 78 may also be a means to differentiate PACs from PVCs using the morphology of R-waves of the cardiac rhythm.

Although processor 70 may generally control the delivery of pacing therapy to treat the detected premature contractions, premature detection module 78 may define therapy delivery according to the type of premature contractions detected. Premature detection module 78 may include one or more processors, similar to processor 70, or may be implemented by processor 70, and processes instructions stored within memory 72 or a separate memory module associated with premature detection module 78. In other examples, premature detection module 78 may be embodied as a list of instructions or software executed by processor 70. Alternatively, premature detection module 78 may be an analog circuit designed to detect PACs and PVCs from the rhythm of heart 12. The differentiation between atrial fibrillation and premature contractions by premature detection module 78 may enable processor 70 to prevent inappropriate delivery of therapy, e.g., cardioversion, upon an inaccurate detection of atrial fibrillation. Delivering therapy to patient 14 upon misdiagnosing premature contractions as atrial fibrillation could cause unintended effects and fail to remedy the premature contractions. Therefore, proper implementation of the diagnosing techniques described herein may allow processor 70 to more appropriately treat a cardiac condition of patient 14. Further, differentiating between PACs and PVCs may provide increased accuracy in diagnosis and effective treatment. Detection of PACs and PVCs occurring above a treatment frequency threshold may allow processor 70 to implement proper pacing therapy. In addition, detection of PVCs occurring at a frequency above a stroke threshold may allow processor 70 to indicate that patient 14 is at increased risk of a stroke.

Based upon the diagnosis of premature contractions and the frequency of those contractions, processor 70 may use instructions stored in memory 72 to deliver pacing therapy designed to reduce or eliminate the premature contractions. Depending upon the type and frequency of premature contractions, processor 70 may implement a single pacing regimen, a recurring pacing regimen, or a tiered pacing regimen to treat patient 14. These different types of pacing therapies are discussed in detail below.

IMD 16 may also include one or more sensors 82 separate from electrodes 40, 42, 46, and 36. Via a signal generated by sensor 82, processor 70 may monitor one or more physiological parameters indicative of cardiac contraction, autonomic tone, heart failure, stroke, and/or ejection fraction. Examples of sensors 82 that may generate a signal indicative of cardiac contraction include a intracardiac or intravascular pressure sensor, an accelerometer or other sensor capable of detecting heart or blood sounds, vibrations, or motion, an optical or ultrasonic sensor capable or detecting changes in flow associated with cardiac contractions, or an optical sensor capable of detecting oxygen saturation changes associated with cardiac contractions. Processor 70 may detect cardiac contractions based on signals from one or more sensors 82, and detect arrhythmias based on the detected cardiac contractions.

Telemetry module 80 includes any suitable hardware, firmware, software or any combination thereof for communicating with another device, such as programmer 24 (FIG. 1). Under the control of processor 70, telemetry module 80 may receive downlink telemetry from and send uplink telemetry to programmer 24 with the aid of an antenna, which may be internal and/or external. Processor 70 may provide the data to be uplinked to programmer 24 and receive downlinked data from programmer 24 via an address/data bus. In some examples, telemetry module 80 may provide received data to processor 70 via a multiplexer.

In some examples, processor 70 transmits indications of detected premature contractions therefrom via telemetry module 80. Processor 70 may also transmit, via telemetry module 80, information regarding pacing stimulation therapy delivered by signal generator 74 and a response to the pacing therapy, e.g., continued detection of premature contractions by electrical sensing module 76.

The various components of IMD 16 are coupled to power source 84, which may include a rechargeable or non-rechargeable battery. A non-rechargeable battery may be capable of holding a charge for several years, while a rechargeable battery may be inductively charged from an external device, e.g., on a daily or weekly basis. In other examples, power source 84 may include a supercapacitor.

Figure 5:
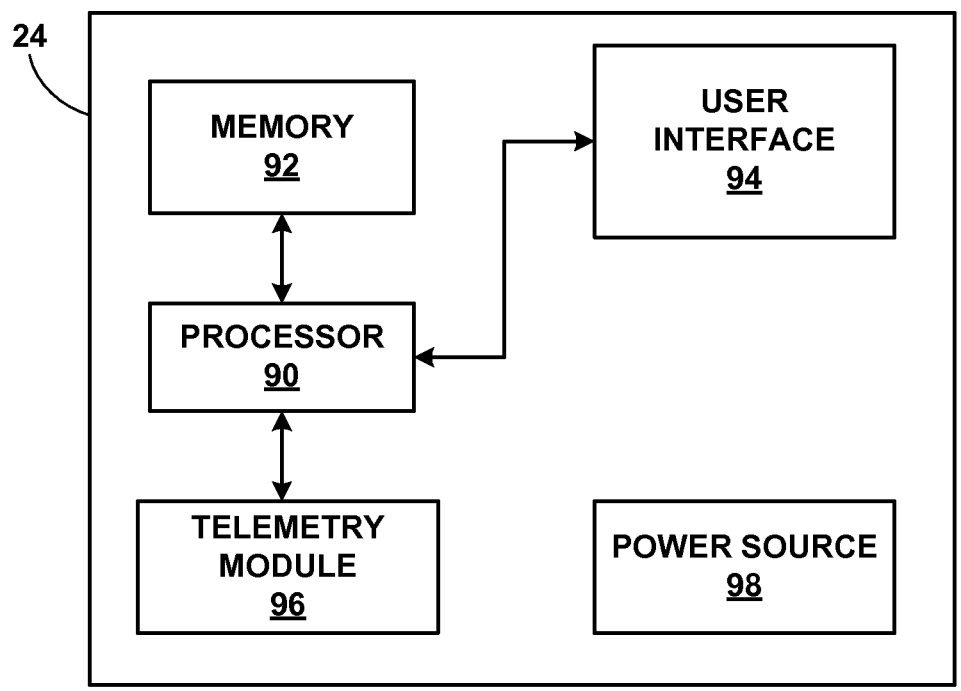
FIG. 5 is block diagram of an example external programmer that facilitates user communication with the IMD.

FIG. 5 is block diagram of an example external programmer 24. As shown in FIG. 5, programmer 24 includes processor 90, memory 92, user interface 94, telemetry module 96, and power source 98. Programmer 24 may be a dedicated hardware device with dedicated software for the programming of IMD 16. Alternatively, programmer 24 may be an off-the-shelf computing device running an application that enables programmer 24 to program IMD 16.

A user may use programmer 24 to select therapy programs (e.g., sets of operational parameters), generate new therapy programs, or modify therapy programs for IMD 16. Programmer 24 may also be used to adjust the detection and diagnosis parameters used by IMD 16 to identify premature contractions within the cardiac rhythm. Programmer 24 may additionally be used to alert the user of detected premature contractions, whether the contractions are PACs or PVCs, any therapy delivered, and/or suggested further treatment of patient 14. Alerts may be pushed to programmer 24 if immediate treatment of patient 14 is required or the alerts may be presented upon the next interrogation or programming session of IMD 16. The clinician may interact with programmer 24 via user interface 94 which may include a display to present a graphical user interface to a user, and a keypad or another mechanism for receiving input from a user.

Processor 90 can take the form one or more microprocessors, DSPs, ASICs, FPGAs, programmable logic circuitry, or the like, and the functions attributed to processor 90 herein may be embodied as hardware, firmware, software or any combination thereof. Memory 92 may store instructions that cause processor 90 to provide the functionality ascribed to programmer 24 herein, and information used by processor 90 to provide the functionality ascribed to programmer 24 herein. Memory 92 may include any fixed or removable magnetic, optical, or electrical media, such as RAM, ROM, CD-ROM, hard or floppy magnetic disks, EEPROM, or the like. Memory 92 may also include a removable memory portion that may be used to provide memory updates or increases in memory capacities. A removable memory may also allow patient data to be easily transferred to another computing device, or to be removed before programmer 24 is used to program therapy for another patient. Memory 92 may also store information that controls premature contraction detection and therapy delivery by IMD 16, such as stimulation parameter values associated with cardiac pacing therapy delivered by signal generator 84 of IMD 16.

Programmer 24 may communicate wirelessly with IMD 16, such as using RF communication or proximal inductive interaction. This wireless communication is possible through the use of telemetry module 96, which may be coupled to an internal antenna or an external antenna. An external antenna that is coupled to programmer 24 may correspond to the programming head that may be placed over heart 12, as described above with reference to FIG. 1. Telemetry module 96 may be similar to telemetry module 96 of IMD 16 (FIG. 4).

Telemetry module 96 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 90 may be configured to provide some or all of the functionality ascribed to processor 70 or premature detection module 78 of IMD 16 herein. For example, processor 90 may receive indications of cardiac depolarizations or contractions, a signal from one or more sensors 82, or information regarding detected premature contractions from IMD 16 via telemetry module 96. In some examples, processor 90 may initiate or modify cardiac pacing therapy for premature contractions by controlling signal generator 74 and sensing module 76 via telemetry modules 96 and 80, as described herein with respect to IMD 16 and processor 70. Alternatively, programmer 24 may include a premature detection module, similar to premature detection module 78, that aids in the detection of premature contractions or depolarizations via generating Lorenz plots, analyzing the morphology of R-waves, or determining coupling intervals.

Figure 6:
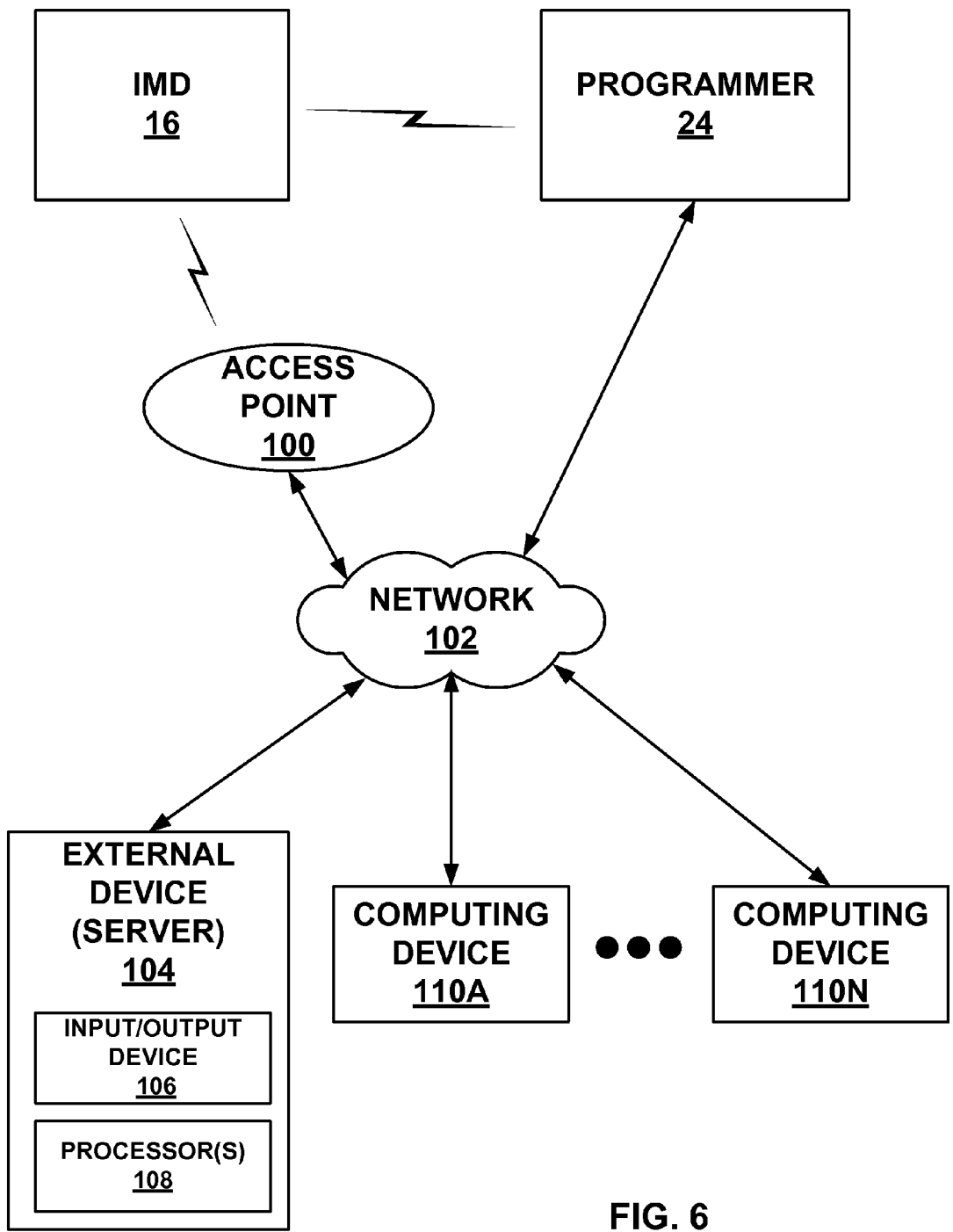
FIG. 6 is a block diagram illustrating an example system that includes an external device, such as a server, and one or more computing devices that are coupled to the IMD and programmer shown in FIG. 1 via a network.

FIG. 6 is a block diagram illustrating an example system that includes an external device, such as a server 104, and one or more computing devices 110A-110N, that are coupled to the IMD 16 and programmer 24 shown in FIG. 1 via a network 102. In this example, IMD 16 may use its telemetry module 80 to communicate with programmer 24 via a first wireless connection, and to communication with an access point 100 via a second wireless connection. In the example of FIG. 6, access point 100, programmer 24, server 104, and computing devices 110A-110N are interconnected, and able to communicate with each other, through network 102. In some cases, one or more of access point 100, programmer 24, server 104, and computing devices 110A-110N may be coupled to network 102 through one or more wireless connections. IMD 16, programmer 24, server 104, and computing devices 110A-110N may each comprise one or more processors, such as one or more microprocessors, DSPs, ASICs, FPGAs, programmable logic circuitry, or the like, that may perform various functions and operations, such as those described above with reference to processor 70 or premature detection module 78 of IMD 16 and processor 90 of programmer 24.

Access point 100 may comprise a device that connects to network 102 via any of a variety of connections, such as telephone dial-up, digital subscriber line (DSL), or cable modem connections. In other examples, access point 100 may be coupled to network 102 through different forms of connections, including wired or wireless connections. In some examples, access point 100 may be co-located with patient 14 and may comprise one or more programming units and/or computing devices (e.g., one or more monitoring units) that may perform various functions and operations described herein. For example, access point 100 may include a home-monitoring unit that is co-located with patient 14 and that may monitor the activity of IMD 16.

In some cases, server 104 may be configured to provide a secure storage site for data that has been collected from IMD 16 and/or programmer 24. Network 102 may comprise a local area network, wide area network, or global network, such as the Internet. In some cases, programmer 24 or server 106 may assemble data in web pages or other documents for viewing by trained professionals, such as clinicians, via viewing terminals associated with computing devices 110A-110N. The illustrated system of FIG. 6 may be implemented, in some aspects, with general network technology and functionality similar to that provided by the Medtronic CareLink® Network developed by Medtronic, Inc., of Minneapolis, Minn.

In some examples, processor 108 of server 104 may be configured to provide some or all of the functionality ascribed to processor 70 of IMD 16 herein. For example, processor 106 may receive indications of cardiac depolarizations or contractions, a signal from one or more sensors 82, or information regarding detected premature contractions via access point 100 or programmer 24 and network 102. Processor 106 may also initiate and/or terminate cardiac pacing therapy, in response to the detected premature contractions, delivered by signal generator 74 of IMD 16. In some examples, server 104 relays received indications of cardiac depolarizations or contractions, a signal from one or more sensors 82, or information regarding detected premature contractions provided by one or more of IMD 16 or programmer 24 to one or more of computing devices 110 via network 102. A processor of a computing device 110 may similarly provide some or all of the functionality ascribed to processor 70 of IMD 16 herein.

FIGS. 7A-C include example cardiac rhythms 120, 130, and 132 of cardiac cycles subject to premature contractions. As shown in FIG. 7A, cardiac rhythm 120 indicates an example cardiac rhythm with premature contractions of the atria, i.e., PACs. PACs may also be referred to as supraventricular premature contractions or supraventricular bigeminism. Peak 122 is a sinus P-wave, peak 124 is an R-wave, and peak 126 is a premature atrial contraction (PAC). The coupling interval between the R-waves of a sinus rhythm, or normal cardiac cycle, and the following PAC is indicated by CI. The R-R interval between R-waves of any cardiac cycles is indicated by RR.

PACs can be detected in the electrocardiogram due to the abnormal and misshapen P-wave indicated by peak 126. However, identifying the misshapen P-wave of peak 126 is not necessarily necessary to differentiate PACs from other premature contractions. Nonetheless, the occurrence PACs result in changing R-R interval lengths as indicated in the example consecutive R-waves within cardiac rhythm 120. PACs create an abnormal cardiac rhythm, but may not be a significant disruption to hemodynamic function of heart 12. Although infrequent PACs may seldom be treated with cardiac pacing therapy, more frequent PACs may benefit from pacing intervention.

As shown in FIG. 7B, cardiac rhythm 130 indicates an example cardiac rhythm with premature contractions of the ventricles, i.e., PVCs. PVCs may also be referred to as ventricular bigeminism. Peak 122 is a sinus P-wave, peak 124 is an natural R-wave as would occur from normal atrioventricular conduction during sinus rhythm, and peak 128 is the R-wave of a premature ventricular contraction (PVC). The coupling interval between the R-waves of a sinus rhythm and the following PVC is indicated by CI. The R-R interval between R-waves of any cardiac cycles is indicated by RR.

PVCs result in R-waves that are dissimilar from normal R-waves in an electrocardiogram, as shown in cardiac rhythm 130. R-waves of PVCs may have different amplitudes, different polarities (e.g., maybe inverted), and different durations that can be shorter or longer than normal R-waves. Similar to PACs, the R-R intervals between consecutive R-waves change between normal cardiac cycles and PVCs. These changes in R-R intervals allow premature contractions to be differentiated from atrial fibrillation with Lorenz plots, as described further in FIGS. 8A, 8B, and 9.

As shown in FIG. 7C, premature contractions may occur with varying frequency in the cardiac rhythm. Cardiac rhythm 132 illustrates examples of R-waves in a normal cardiac cycle, with one such R-wave being labeled as R-wave 124 and examples of R-waves resulting from PVCs, with one such R-wave being labeled as R-wave 128. In the example of cardiac rhythm 132, PVCs are occurring at a 33% rate because the PVC R-waves 128 occur once for every three total R-waves. In other words, one PVC is occurring for every two normal cardiac cycles. PVCs may occur in any frequency, from only once or twice in thousands of cardiac cycles to every other cardiac cycle, i.e., continuous bigeminism. Typically, PVCs occurring at a 50% rate or higher may be labeled as bigeminy, and such a frequency may compromise hemodynamics sufficiently for pacing therapy intervention.

Since more frequent PVCs can put patient 14 at risk of heart failure, heart failure deterioration, or even stroke, some type of intervention may be beneficial. If pacing therapy is not provided by IMD 16, IMD 16 may present an alert anytime PVCs have been detected or when the PVC frequency has surpassed a present frequency threshold. An example alert frequency threshold may generally be between approximately 5% and 30% PVC occurrence. An example therapy frequency threshold may generally be between approximately 10% and 50% PVC occurrence. However, the alert frequency threshold or therapy frequency threshold for IMD 16 may be set to any value desired by the user in other examples.

PVC detection may be desired because patient 14 may be at higher risk of stroke and left ventricular dilation when the frequency of PVCs surpasses 24%. When PVCs occur at this frequency, circulation is compromised and blood may pool within the left ventricle. In response, PVCs may lead to cardiomyopathy and left ventricular enlargement. In one example, IMD 16 may provide pacing therapy, or drug therapy, to suppress PVCs once the frequency exceeds 10%. In addition or as an alternative to therapy, IMD 16 may present an alert that suggests patient 14 be examined for heart 12 damage or other risk factors for stroke.

Although cardiac rhythm 132 illustrates PVC frequency, similar premature contraction frequencies may occur with PACs. The frequency of PACs may indicate when patient 14 is at risk of entering atrial fibrillation. Although IMD 16 may provide an alert to a user that indicates PACs could lead to atrial fibrillation, IMD 16 may in other examples provide cardiac pacing therapy to reduce the prevalence of PACs.

Figure 8B:
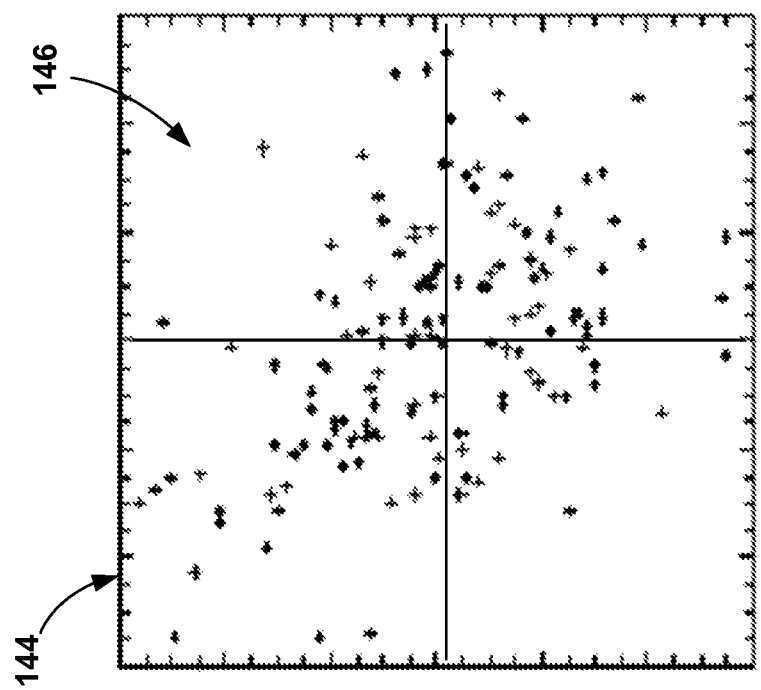
FIGS. 8A and 8B are example Lorenz plots of changes in R-R intervals that indicate a sinus rhythm and atrial fibrillation, respectively.
Figure 8A:
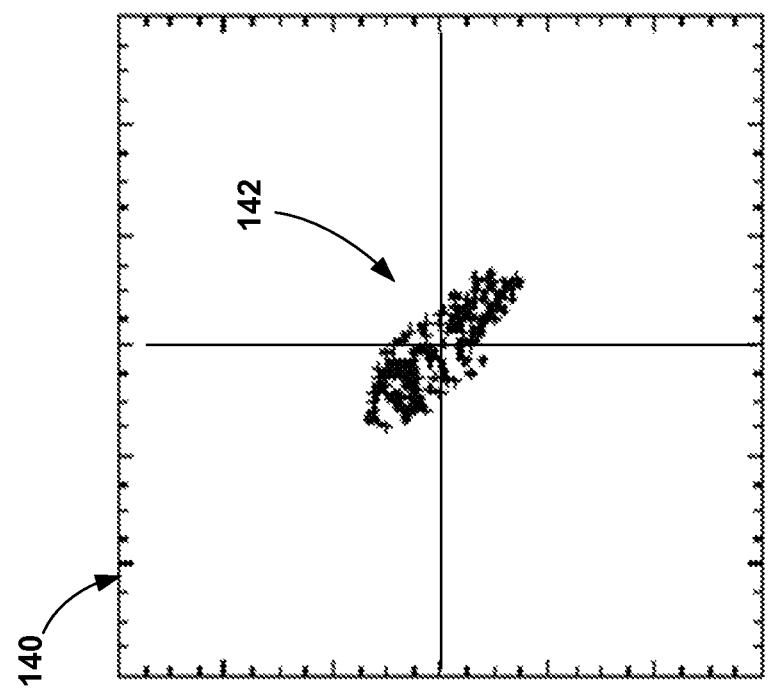

FIGS. 8A and 8B are example Lorenz plots 140 and 144, respectively, of changes in R-R intervals that indicate a sinus rhythm and atrial fibrillation, respectively. As shown in FIG. 8A, Lorenz plot 140 provides a plot of changes in R-R intervals between consecutive cardiac cycles. Points 142 are localized around the origin of Lorenz plot 140 with little variation between each point. In this example, Lorenz plot 140 of points 142 indicates a normal sinus rhythm because the degree of variability in cardiac cycle lengths is very minimal. No premature contractions are present and heart 12 is functioning normally.

In contrast, FIG. 8B illustrates an example Lorenz plot 144 indicating atrial fibrillation of heart 12. Points 146 are scattered throughout all four quadrants of Lorenz plot 144, indicating that the R-R interval changes are constantly changing between each cardiac cycle. The degree of variability of cardiac cycle lengths is very high with atrial fibrillation because the R-R interval changes are highly scattered. These constantly changing R-R intervals are typical in atrial fibrillation which involves erratic heart beats. In this manner, IMD 16, or premature detection module 78, may differentiate between atrial fibrillation and sinus rhythms, and IMD 16 may provide appropriate therapy.

Figure 9:
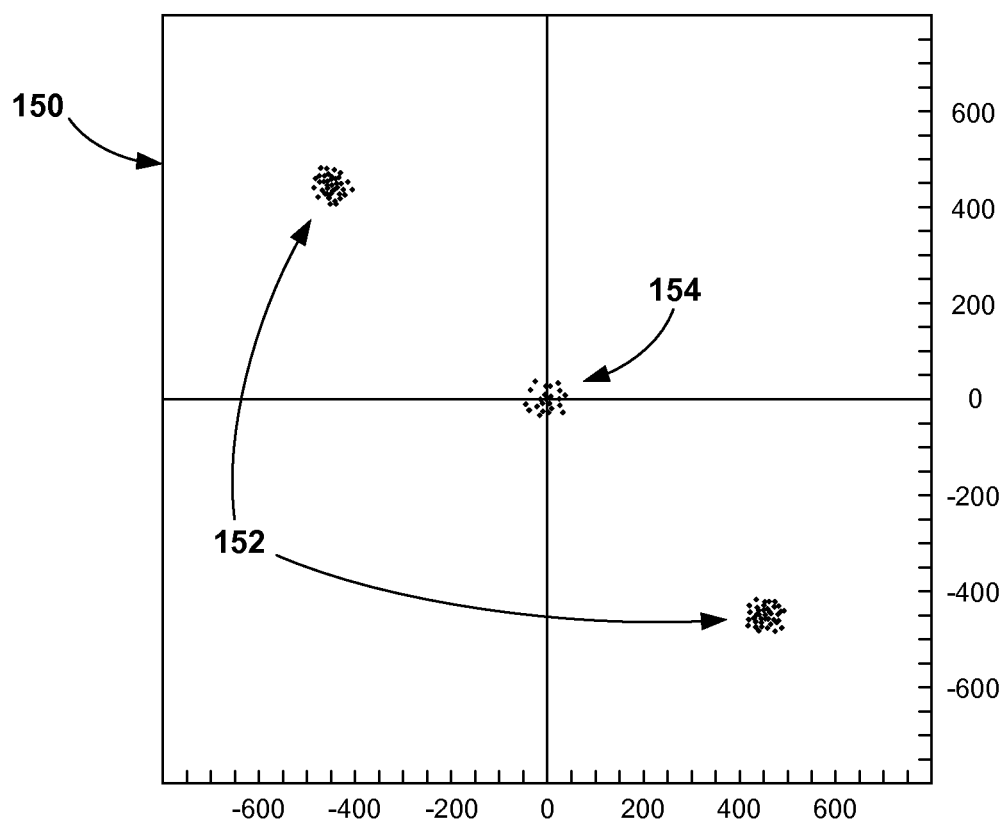
FIG. 9 is an example Lorenz plot of changes in R-R intervals that indicate bigeminy.

FIG. 9 is an example Lorenz plot 150 of changes in R-R intervals that indicates bigeminism. As shown in FIG. 9, Lorenz plot 150 provides a plot of changes in R-R intervals between consecutive cardiac cycles. Lorenz plot 150 includes points 152 of R-R interval changes clustered far from the origin of the plot and in opposite quadrants of Lorenz plot 150. Points 152 are illustrative of premature contractions, e.g., PACs or PVCs, occurring during a cardiac rhythm. In other words, points 152 result from consistent changes in R-R intervals between consecutive cardiac cycles. Although there is variability between cardiac cycle lengths, there is a moderate degree of variability because R-R interval changes are localized to only a few positions in the Lorenz plot. Points 154 are indicative of normal cardiac cycles within the cardiac rhythm because there were no changes in the R-R interval between some consecutive cardiac cycles.

Since points 154 indicate some normal cardiac cycles, Lorenz plot 150 is typical of frequent, but intermittent, premature contractions. If Lorenz plot 150 only includes points 152, the cardiac rhythm would be considered as continuous bigeminism, or premature contractions occurring 50% of the time. It should be noted that although a Lorenz plot may be able to differentiate between premature contractions and atrial fibrillation, a Lorenz plot alone may not be able to differentiate between PACs and PVCs. Although IMD 16 may provide cardiac pacing therapy based solely upon a Lorenz plot, additional information may be desirable to diagnose the premature contractions as either PACs or PVCs.

Figure 10:
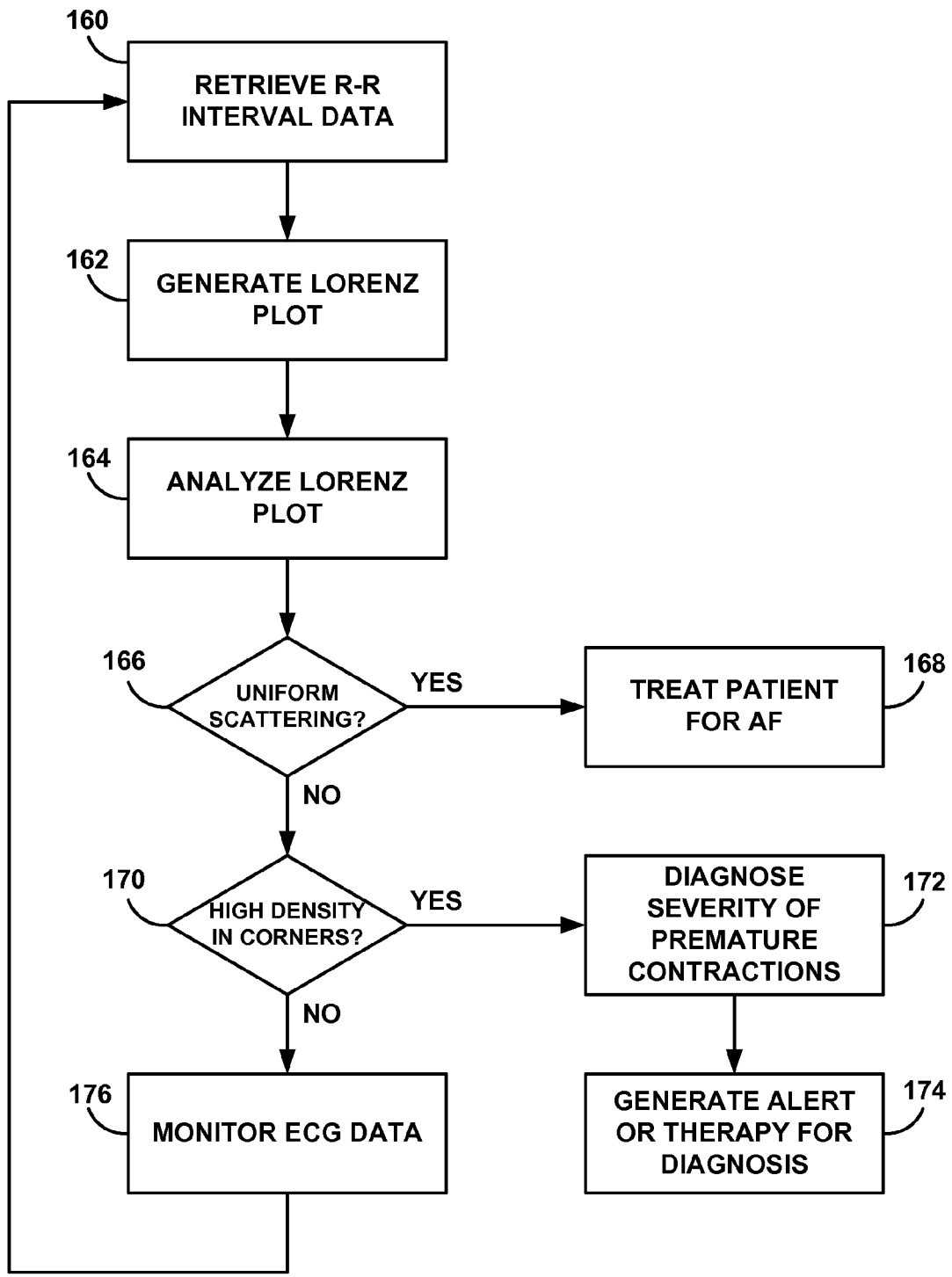
FIGS. 10-12 are flow diagrams of example methods for diagnosing premature contractions from cardiac rhythms.
Figure 11:
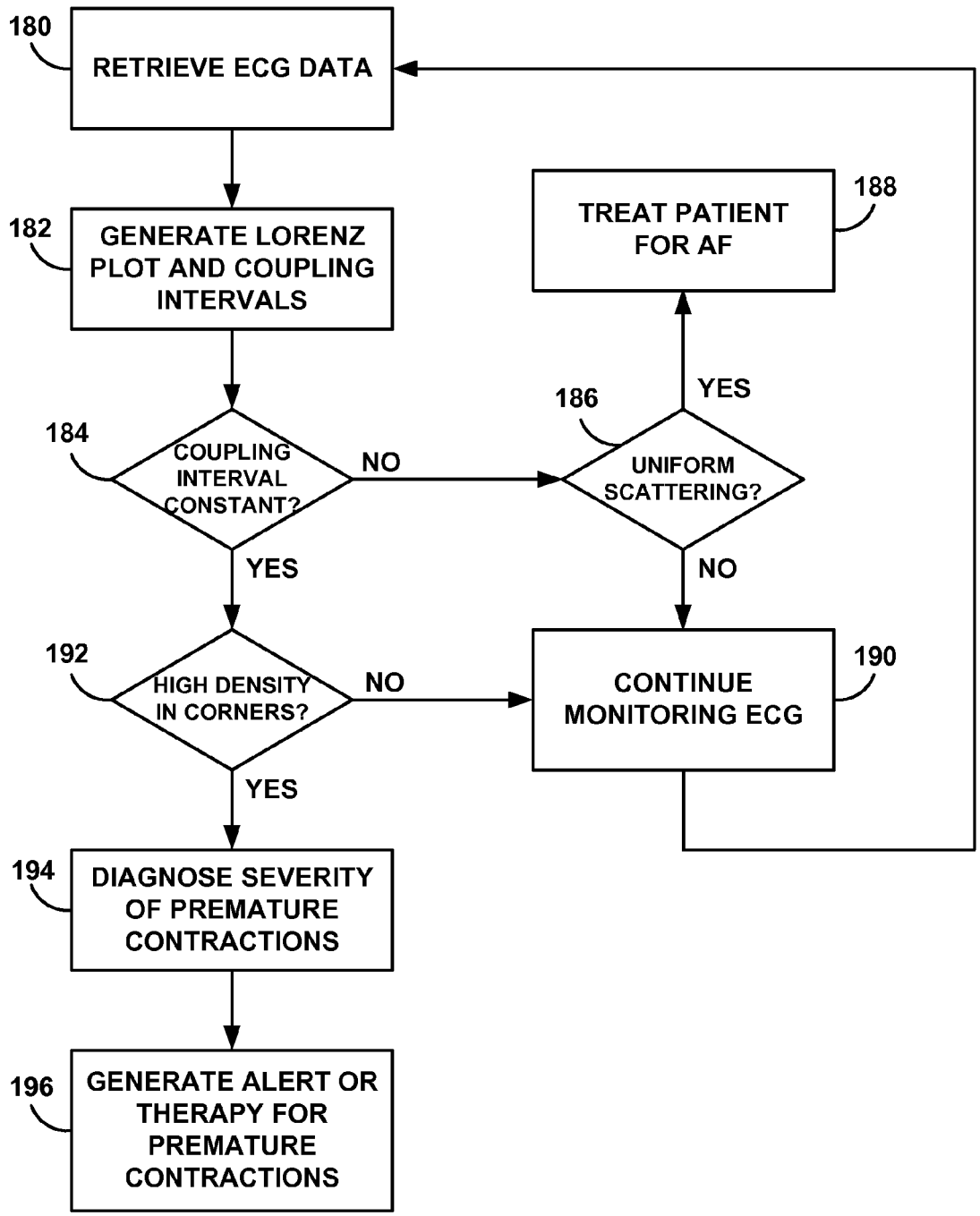
Figure 12:
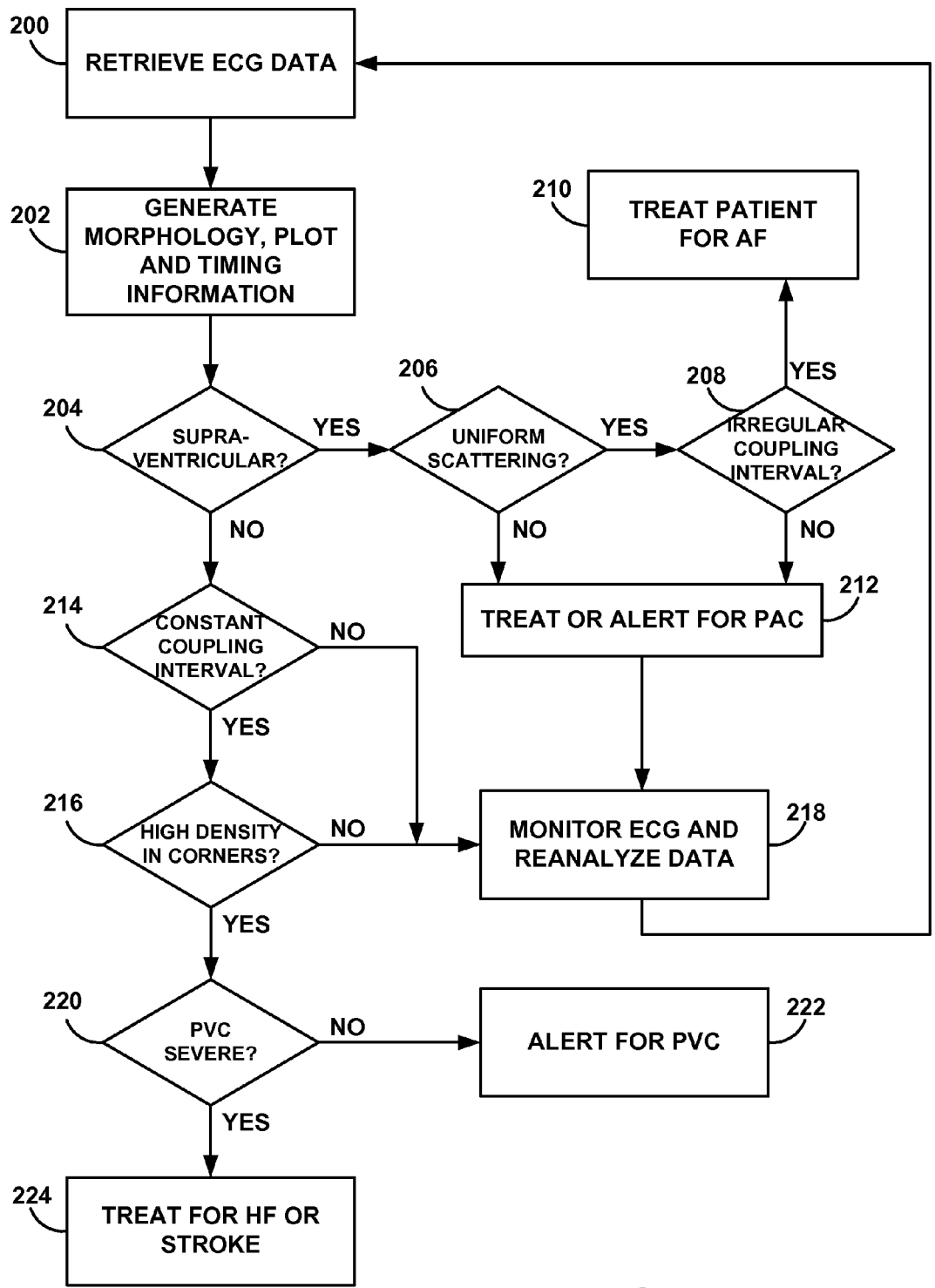

FIGS. 10-12 are flow diagrams of example methods for diagnosing premature contractions from other cardiac rhythms. IMD 16 generally monitors heart 12 for cardiac cycle lengths to diagnose premature cardiac events, e.g., atrial or ventricular contractions, through determination of the degree of variability between cardiac cycle lengths. In general, IMD 16 may monitor the cardiac rhythm intermittently, but some examples of IMD 16 may continuously, or in real-time, monitor the cardiac rhythm for premature contractions. As shown in FIG. 10, premature detection module 78, with the aid of processor 70 of IMD 16, begins the diagnosis of cardiac rhythms by retrieving R-R interval data from memory 72 or directly from sensing module 76 (160). Whether the R-R intervals are retrieved from memory 72 or sensing module 76 may depend upon the real-time or post processing detection, where real-time detection may require depolarization data to be directly sent from sensing module 76 to premature detection module 78.

Premature detection module 78 then generates a Lorenz plot of the changes in R-R intervals based upon the intervals received or more complete cardio-electrogram information (162). The Lorenz plot may be used to identify contraction variability with changes in R-wave intervals between successive contractions. The Lorentz plot may include R-R intervals during a certain number of cardiac cycles or for a predetermined amount of time. In real-time monitoring, for example, the Lorenz plot may be continually updated on a rolling basis to include the most recent period of time, e.g., the last 10 minutes, or the most recent number of cardiac cycles. Premature detection module 78 then analyzes the Lorenz plot to differentiate premature contractions from atrial fibrillation, sinus rhythms, or other cardiac rhythms (164). If the points within the Lorenz plot are scattered uniformly about the Lorenz plot and the degree of variability is high (166), then premature detection module 78 diagnoses the cardiac rhythm as atrial fibrillation (AF) and commands processor 70 to treat patient 14, e.g., deliver a defibrillation stimulus (168).

If there is no uniform scattering of R-R interval changes (166), premature detection module 78 analyzes the Lorenz plot for a high density or cluster of R-R interval changes far from the origin and in opposite quadrants of the Lorenz plot (170). If there is a high density of points in the corners of the plot, i.e., in opposite quadrants, premature detection module 78 then determines there is a moderate degree of variability and diagnoses the severity of the premature contractions (172). For example, a high density of points may be set as greater than 40% of all points on the plot. However, this density threshold may be dependent upon the total number of points used to create the Lorenz plot. The severity of the premature contractions may be determined based upon the percentage of points clustered far in opposing quadrants. Premature detection module 78, or processor 70, may then generate an alert regarding the premature contractions or deliver cardiac pacing therapy depending upon the severity of the premature contractions in the cardiac rhythm (174). In alternative examples, premature detection module 78 may not determine the severity, or frequency, of premature contractions with the Lorentz plot.

If there is no uniform scattering (166) and no high density of points (170) in the Lorenz plot, premature detection module 78 may simply continue monitoring cardio-electrogram data for problematic rhythms (160). An absence of scattering and high densities in opposing quadrants indicates a minimal degree of variability in cycle lengths and that a normal sinus rhythm is being produced by heart 12.

As shown in FIG. 11, premature detection module 78, with the aid of processor 70 of IMD 16, begins the diagnosis of cardiac rhythms by retrieving R-R interval data from memory 72 or directly from sensing module 76 (180). As described in FIG. 10, whether the R-R intervals are retrieved from memory 72 or sensing module 76 may depend upon the real-time or post processing detection, where real-time detection may require cardio-electrogram data to be directly sent from sensing module 76 to premature detection module 78.

Premature detection module 78 then generates a Lorenz plot of the changes in R-R intervals and coupling intervals based upon the intervals received or more complete cardio-electrogram information (182). If the coupling interval is not constant (184), premature detection module 78 analyzes the Lorenz plot for uniform scattering throughout the plot (186). The Lorentz plot may include R-R intervals during a certain number of cardiac cycles or for a predetermined amount of time. In real-time monitoring, for example, the Lorenz plot may be continually updated on a rolling basis to include the most recent period of time, e.g., the last 10 minutes, or the most recent number of cardiac cycles. Premature detection module 78 then analyzes the Lorenz plot to differentiate premature contractions from atrial fibrillation, sinus rhythms, or other cardiac rhythms (186). If the points within the Lorenz plot are scattered uniformly about the Lorenz plot to indicate a high degree of variability in cardiac lengths (186), then premature detection module 78 diagnoses the cardiac rhythm as atrial fibrillation (AF) and commands processor 70 to treat patient 14, e.g., deliver a defibrillation stimulus (188).

If there is a constant coupling interval (184) and a high density or cluster of R-R interval changes far from the origin and in opposite quadrants of the Lorenz plot (192), premature detection module 78 determines that there is a moderate degree of variability in cardiac cycle lengths and diagnoses the cardiac rhythm as including premature contractions and evaluates the severity of the contractions using the density of the points in the Lorenz plot (194). For example, a high density of points may be set as greater than 40% of all points on the plot. However, this density threshold may be dependent upon the total number of points used to create the Lorenz plot. The severity of the premature contractions may be determined based upon the percentage of points clustered far in opposing quadrants. Premature detection module 78, or processor 70, may then generate an alert regarding the premature contractions or deliver cardiac pacing therapy depending upon the severity of the premature contractions in the cardiac rhythm (174). In alternative examples, premature detection module 78 may not determine the severity, or frequency, of premature contractions with the Lorentz plot.

If there is neither a uniform scattering of points in the Lorenz plot (186) nor a high density of points in opposite quadrants (192), then premature detection module 78 may determine that there is a minimal degree of variability in cardiac cycle length and continue monitoring the cardiac rhythm (190). Premature detection module 78 may continue to retrieve cardio-electrogram data (180).

As shown in FIG. 12, premature detection module 78 is capable of diagnosing between PACs and PVCs. Premature detection module 78, with the aid of processor 70 of IMD 16, begins the diagnosis of cardiac rhythms by retrieving cardio-electrogram data from memory 72 or directly from sensing module 76 (200). As described in FIGS. 10 and 11, whether the R-R intervals are retrieved from memory 72 or sensing module 76 may depend upon the real-time or post processing detection, where real-time detection may require cardio-electrogram data to be directly sent from sensing module 76 to premature detection module 78.

Premature detection module 78 then generates a Lorenz plot of the changes in R-R interval, coupling intervals based upon the intervals received or more complete cardio-electrogram information, and morphology information from the same cardiac cycles (202). Premature detection module 78 analyzes the morphology of each cardiac cycle, e.g. each R-wave, to determine the amplitude, polarity, and duration of the R-waves. Similar amplitudes, polarities (positive or negative amplitudes), and durations suggest that premature contractions, if any, are supraventricular and occurring in the atria and classified as PACs. R-waves having different amplitudes, polarities (positive or negative amplitudes), and durations indicate that premature contractions would be originating in the ventricles and classified as PVCs. If premature detection module 78 identifies the possible premature contractions as supraventricular (204), then the premature detection module 78 analyzes the Lorenz plot and coupling intervals of the cardiac cycles. If the R-R interval changes in the Lorenz plot are uniformly scattered throughout the plot with a high degree of cardiac cycle variability (206) and the measured coupling interval is irregular (208), then processor 70 may treat patient 14 for atrial fibrillation since the contractions are not premature. (210).

If there is no uniform scattering in the Lorenz plot (206) and constant coupling intervals within the cardiac rhythm (208), then premature detection module 78 has identified PACs and may instruct processor 70 to alert a user of the condition or treat patient 14 to remedy the PACs (212). More frequent PACs may be indicative of increased atrial fibrillation risk, so an alert may be generated upon a predetermined PAC frequency threshold. As one example, an alert may be generated when the PAC frequency reaches a 10% threshold. In other examples, the alert may be generated within lower or higher frequency thresholds. Alternatively, processor 70 may deliver cardiac pacing therapy when the PAC frequency surpasses a PAC frequency threshold. For example, processor 70 may deliver cardiac pacing therapy when the PAC frequency threshold reaches 25%.

If the morphology of the R-waves indicates that any premature contractions are ventricular (204), premature detection module 78 proceeds to analyze the coupling intervals and Lorenz plot. If the coupling interval is not constant (214) or there are no high density clusters in opposing quadrants of the Lorenz plot (216), then the low degree of variability indicates that no premature contractions have been identified and premature detection module 78 continues to monitor the cardio-electrogram data for potential premature contractions evident in the contraction timing of other cardiac rhythms (218).

If premature detection module 78 identifies the coupling intervals as constant (214) and there are high density locations of R-R interval changes in opposing quadrants of the Lorenz plot for a moderate degree of variability in cardiac cycle lengths (216), premature detection module 78 diagnoses the cardiac rhythm as including PVCs. Premature detection module 78 then determines the severity of the PVCs based upon the frequency of the PVCs within the cardiac rhythm (220). If the PVCs are not severe (220), premature detection module 78 may signal processor 70 to alert the user of the presence of PVCs in the cardiac rhythm of patient 14 (222). If the PVCs are severe, e.g., patient 14 is suffering from bigeminy, premature detection module 78 may signal for processor 70 to treat patient 14 with cardiac pacing therapy (224). Cardiac pacing therapy may be provided to restart normal intrinsic pacing, e.g., a sinus rhythm. The PVC therapy threshold that indicates whether the PVCs are severe may be set to 10% PVCs in one example. However, the therapy threshold may be set to any percentage, such as an example range of 5% to 50% PVC frequency. Although premature detection module 78 may signal an alert any time a PVC is detected, generally the alert may only be delivered when the PVC frequency rises above an alert threshold. An example alert threshold may be a 5% PVC frequency. In this manner, premature detection module 78 may deliver cardiac pacing therapy and deliver an alert identifying the detected PVCs. After an alert and/or therapy has been delivered, premature detection module 78 may continue to analyze cardio-electrogram information and identify premature contractions (200).

Although diagnosis of premature contractions has been generally described in FIGS. 10-12 for a single chamber cardiac device, e.g., IMD 16 and a single lead, dual chamber cardiac device may also utilize the same techniques to diagnose premature contractions. However, in some examples, a dual chamber or multi-chamber device may be capable of diagnosing premature contractions with alternative techniques.

In a multi-chamber cardiac device with atrioventricular sensing capabilities, e.g., system 50 of FIG. 3, diagnosing premature contractions may be more straightforward. For example, the coupling intervals measured in either the atria or ventricles may each be identified as constant or irregular. Irregular coupling intervals indicate intermittent PACs or PVCs, and constant coupling intervals indicate the more severe atrial and ventricular bigeminism. In another example, the multi-chambered cardiac device may use a Lorenz plot of R-R intervals detected in the atria for ventricle to determine PACs or PVCs.

Figure 13:
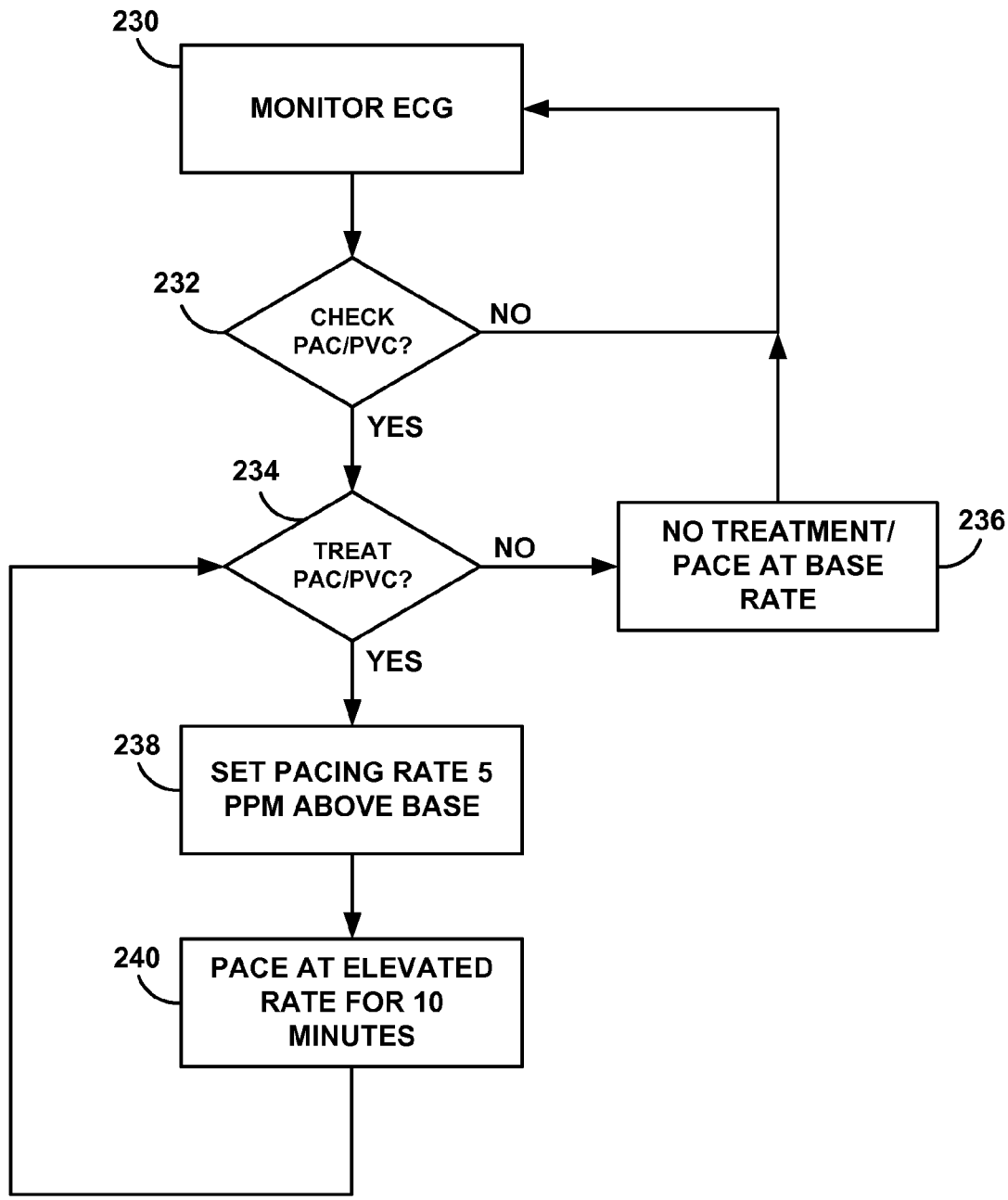
FIGS. 13-14 are flow diagrams of example methods for treating detected premature contractions.
Figure 14:
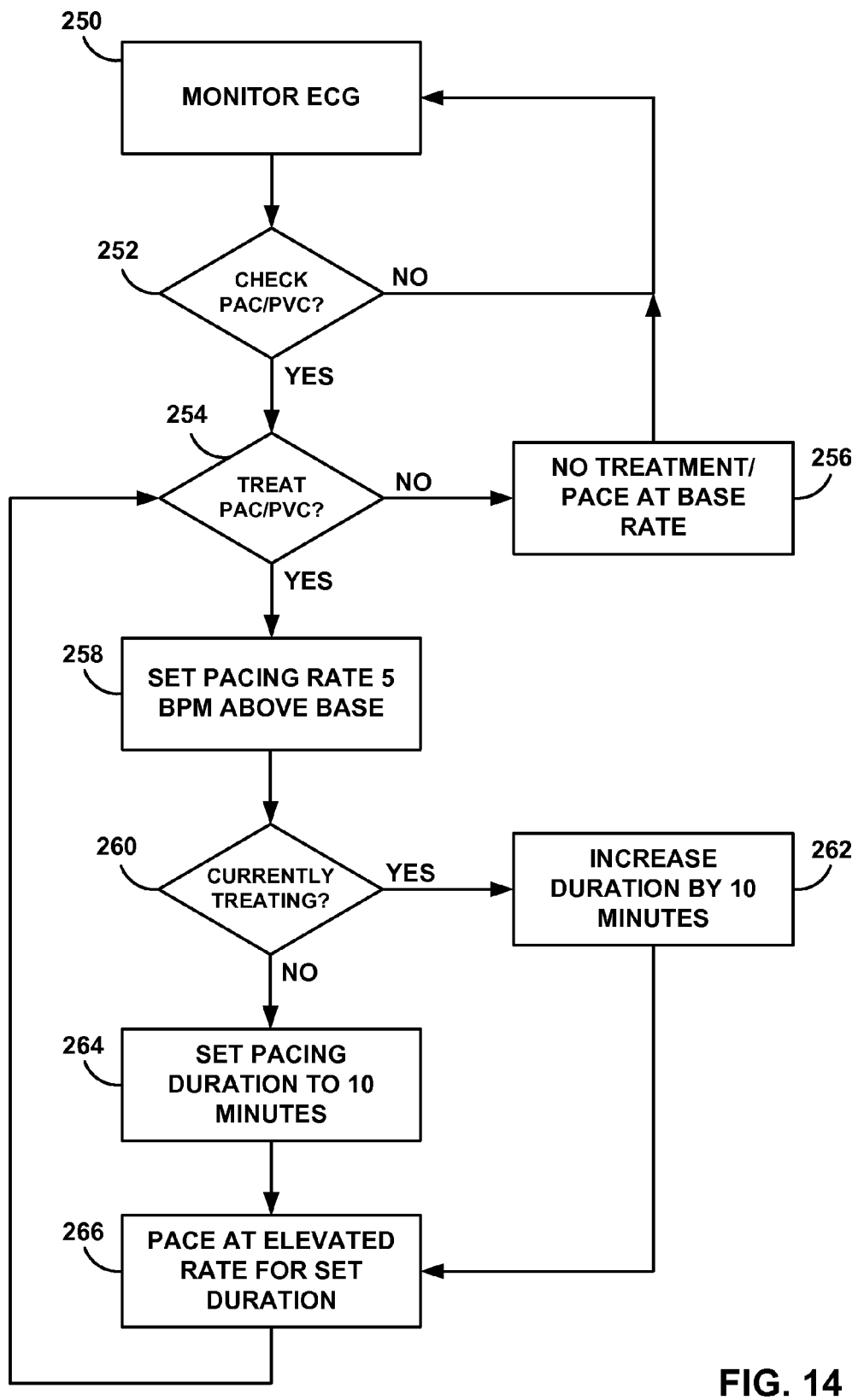

FIGS. 13-14 are flow diagrams of example methods for treating detected premature contractions. In the example of FIG. 13, premature detection module 78 of IMD 16 monitors the cardio-electrogram of heart 12 (230). In some examples, premature detection module 78 may only monitor one characteristic of the cardio-electrogram, such as the R-R interval, when monitoring the contraction timing of heart 12. When premature detection module 78 is signaled to check for the presence of premature contractions (232), premature detection module 78 diagnoses the cardiac rhythm and whether any premature contractions, e.g., PACs or PVCs, need to be treated (234). If there are no premature contractions or the PACs or PVCs are too infrequent to require treatment (234), then processor 70 continues to pace at the predetermined base heart rate or continues to simply monitor patient 14 (230).

If premature detection module 78 indicates that premature contractions are present at a frequency requiring pacing therapy, e.g., the frequency is above the therapy threshold (234), then processor 70 sets the cardiac pacing rate to 5 beats per minute (bpm) above the base pacing rate set for patient 14 (238). For example, if a clinician has set the base or normal heart rate for patient 14 to be 70 beats per minute, then the increased pacing rate is set to 75 ppm. Processor 70 then delivers cardiac pacing therapy at the elevated rate for a 10 minute duration (240). After 10 minutes, premature detection module 78 determines if PACs or PVCs remain in the cardiac rhythm that still requires treatment (234). Although processor 70 may cease pacing therapy to check for premature contractions, other examples may allow form therapy to continue while diagnosis the intrinsic cardiac rhythm for continued premature contractions.

The increase in pacing rate and duration for elevated pacing therapy may be set to any value desired by the clinician or determined by premature detection module 78 based upon the frequency of PACs or PVCs. For example, the increase in pacing rate may be generally between approximately 1 ppm and 20 ppm. However, higher increases in pacing rate are also contemplated. Even with an increased rate to be used, the elevated pacing rate may be limited to a maximum heart rate set by the clinician for patient 14. In general, the elevated pacing rate duration may be between approximately 5 minutes and 60 minutes. However, the elevated pacing rate may be set as long as several hours, days, or even weeks for persistent premature contractions.

In the example of FIG. 14, premature detection module 78 of IMD 16 monitors the cardio-electrogram of heart 12 for contraction timing (250) with the ability to deliver tiered pacing therapy. In some examples, premature detection module 78 may only monitor one characteristic of the cardio-electrogram, such as the R-R interval, when monitoring the contraction timing of heart 12. When premature detection module 78 is signaled to check for the presence of premature contractions (252), premature detection module 78 diagnoses the cardiac rhythm and whether any premature contractions, e.g., PACs or PVCs, need to be treated (254). If there are no premature contractions or the PACs or PVCs are too infrequent to require treatment (254), then processor 70 continues to pace at the predetermined base heart rate or continues to simply monitor patient 14 (250).

If premature detection module 78 indicates that premature contractions are present at a frequency requiring pacing therapy, e.g., the frequency is above the therapy threshold (254), then processor 70 sets the cardiac pacing rate to 5 beats per minute (bpm) above the base pacing rate set for patient 14 (258). For example, if a clinician has set the base or normal heart rate for patient 14 to be 70 beats per minute, then the increased pacing rate is set to 75 bpm. Processor 70 next determines if patient 14 is already being treated for premature contractions with pacing therapy (260). If there is no current therapy (260), processor sets the pacing therapy duration to 10 minutes (264). If there is current therapy being delivered, then processor 70 increased the duration of therapy by 10 minutes (262). This increase in pacing duration may be implemented because the previous therapy was ineffective. Therefore, longer pacing may be required to eliminate the premature contractions within heart 12. In some examples, a maximum duration for increased pacing may be set. If the maximum duration is met, the duration may continue to be set at the maximum duration. Once the pacing duration is set, processor 70 delivers elevated cardiac pacing therapy for the set duration (266). Premature detection module 78 may then reanalyze the cardiac rhythm for any remaining premature contractions.

In general, each increase in pacing duration may be incremental such that every increase is equivalent. In other examples, the incremental increases in duration may be progressive to reach an effective therapy duration in fewer iterations. In any case, the elevated pacing rate duration increment may be between approximately 5 minutes and 60 minutes. However, duration increments may be set to shorter or longer lengths, e.g., hours or days. Alternatively, the increment duration may be determined automatically by processor 70 based upon the frequency of premature contractions. For example, higher frequency premature contractions may require higher increments to treat patient 14.

Alternatively, or additionally, tiered pacing therapy may include an incremental pacing rate approach. When pacing therapy is ineffective at eliminating premature contractions, processor 70 may further increase the pacing rate in the next iteration. For example, if a previous elevated pacing rate of 75 bpm does not eliminate premature contractions from the cardiac rhythm, processor 70 may increment the pacing rate to 80 ppm for the next iteration of pacing therapy. This process may continue until premature contractions are eliminated or a maximum heart rate is reached. In other examples, the pacing rate increments may also be progressive, as discussed above with regard to the pacing duration. Generally, the pacing rate increments may be between approximately 1 ppm and 20 ppm. However, any rate increment may be used based upon clinician programming and/or the severity of premature contractions detected.

The techniques described herein allow an IMD to monitor cardiac rhythms for premature contractions. This diagnosis of premature contractions may allow the IMD to differentiate premature contractions from atrial fibrillation and avoid defibrillation when it is not needed. In addition, these techniques allow an IMD to detect potentially damaging PACs that may lead to atrial fibrillation and PVCs with may lead to atrial fibrillation, heart failure, or even stroke. By diagnosing the premature contractions, the IMD may provide the most appropriate therapy and even reduce a patient's risk of serious health problems by delivering minimal intervention.

Various examples have been described that include diagnosing premature contractions from cardiac rhythms. These examples include techniques for differentiating premature contractions from atrial fibrillation and PACs from PVCs. In addition, cardiac pacing therapy may be provided to reduce the frequency of or eliminate premature contractions from the cardiac rhythm. Any combination of detection and therapy for premature contractions is contemplated. These and other examples are within the scope of the following claims.

The invention claimed is:
1. A method comprising:
monitoring a heart of a patient for cardiac cycle lengths;
determining a degree of variability of the cardiac cycle lengths;
automatically differentiating, by a processor, premature cardiac events from atrial fibrillation based on the determined degree of variability;
analyzing, by the processor, a morphology of the premature cardiac events, wherein analyzing the morphology of the premature cardiac events comprises analyzing the morphology of the premature cardiac events to identify similarity of R-wave amplitude, polarity, and duration;
differentiating, by the processor, premature atrial contractions from premature ventricular contractions based on the analysis, wherein the premature cardiac events comprise at least one of the premature atrial contractions and the premature ventricular contractions;
measuring a coupling interval between R-waves; and
identifying the premature cardiac events as premature ventricular contractions when the analysis includes R-waves of differing amplitude, polarity, and duration and the measurement indicates a constant coupling interval.
2. The method of claim 1, wherein:
the degree of variability is determined by changes in cardiac cycle lengths plotted on a Lorenz plot;
cardiac cycle length changes due to premature cardiac events are clustered in two locations opposite each other and within opposing quadrants of the Lorenz plot; and
cardiac cycle length changes due to atrial fibrillation are scattered throughout the Lorenz plot.
3. The method of claim 1, wherein monitoring the heart comprises detecting a cardio-electrogram with a single lead of a single chamber cardiac therapy device.
4. The method of claim 1, further comprising presenting an alert to a user that at least one of identifies the detected premature cardiac events as premature atrial contractions or premature ventricular contractions, or identifies whether the patient is at risk of heart failure or stroke.
5. The method of claim 1, further comprising delivering cardiac pacing therapy at an increased pacing rate upon detecting premature cardiac events.
6. The method of claim 5, further comprising incrementally increasing the pacing rate until the cardiac pacing therapy eliminates the premature cardiac events.
7. The method of claim 5, further comprising incrementally increasing a duration of the cardiac pacing therapy at the increased pacing rate until the increased pacing rate of the cardiac pacing therapy eliminates the premature cardiac events.
8. The method of claim 1, wherein the premature cardiac events comprise R-waves.
9. The method of claim 1,
further comprising identifying the premature cardiac events as premature atrial contractions when the analysis includes R-waves of similar amplitude, polarity, and duration and the measurement indicates a constant coupling interval.

10. A system comprising:
an implantable medical device configured to monitor a heart of a patient for cardiac cycle lengths; and
a premature detection module configured to:
   determine a degree of variability of the cardiac cycle lengths;
   automatically differentiate premature cardiac events from atrial fibrillation based upon the determined degree of variability;
   analyze a morphology of the premature cardiac events to identify similarity of R-wave amplitude, polarity, and duration;
   differentiate premature atrial contractions from premature ventricular contractions based on the analysis, wherein the premature cardiac events comprise at least one of the premature atrial contractions and the premature ventricular contractions;
   measure a coupling interval between R-waves; and
   identify the premature cardiac events as premature ventricular contractions when the analysis includes R-waves of differing amplitude, polarity, and duration and the measurement indicates a constant coupling interval.

11. The system of claim 10, wherein:
the premature detection module is configured to generate a Lorenz plot of changes in cardiac cycle lengths to determine the degree of variability;
cardiac cycle length changes due to premature cardiac events are clustered in two locations opposite each other and within opposing quadrants of the Lorenz plot; and
cardiac cycle length changes due to atrial fibrillation are scattered throughout the Lorenz plot.

12. The system of claim 10, wherein:
the implantable medical device is a single chamber cardiac therapy device; and
the premature detection module is configured to analyze a cardio-electrogram to monitor the heart.

13. The system of claim 10, further comprising:
a telemetry module within the implantable medical device and configured to transmit an alert that at least one of identifies the detected premature cardiac events as premature atrial contractions or premature ventricular contractions and identify whether the patient is at risk of heart failure or stroke; and
an external programmer configured to present the alert to a user.

14. The system of claim 10, further comprising:
a signal generator configured to generate a cardiac pacing therapy at an increased pacing rate upon detecting premature cardiac events;
one or more electrodes coupled to the signal generator and configured to at least partially deliver the cardiac pacing therapy; and
a processor configured to set the increased pacing rate above a base pacing rate upon detecting premature cardiac events.

15. The system of claim 14, wherein the processor is configured to at least one of incrementally increase the pacing rate and incrementally increase a duration of the cardiac pacing therapy at the increased pacing rate until the increased pacing rate of the cardiac pacing therapy eliminates the premature contractions.

16. The system of claim 10, wherein the premature cardiac events comprise R-waves.

17. The system of claim 10, wherein the premature detection module is configured to:
identify the premature cardiac events as premature atrial contractions when the analysis includes R-waves of similar amplitude, polarity, and duration and the measurement indicates a constant coupling interval.

18. A system comprising:
means for monitoring a heart of a patient for cardiac cycle lengths;
means for determining a degree of variability of the cardiac cycle lengths;
means for automatically differentiating premature cardiac events from atrial fibrillation based upon the determined degree of variability;
means for analyzing a morphology of the premature cardiac events, wherein the means for analyzing the morphology of the premature cardiac events comprises means for analyzing the morphology of the premature cardiac events to identify similarity of R-wave amplitude, polarity, and duration;
means for differentiating premature atrial contractions from premature ventricular contractions based on the analysis, wherein the premature cardiac events comprise at least one of the premature atrial contractions and the premature ventricular contractions;
means for measuring a coupling interval between R-waves; and
means for identifying the premature cardiac events as premature ventricular contractions when the analysis includes R-waves of differing amplitude, polarity, and duration and the measurement indicates a constant coupling interval.

19. The system of claim 18, further comprising means for delivering cardiac pacing therapy at an increased pacing rate upon detecting premature cardiac events.

20. The system of claim 18, further comprising
means for identifying the premature cardiac events as premature atrial contractions when the analysis includes R-waves of similar amplitude, polarity, and duration and the measurement indicates a constant coupling interval.

* * * * *